United States Patent
Lavi et al.

(10) Patent No.: US 11,076,770 B2
(45) Date of Patent: Aug. 3, 2021

(54) SYSTEM FOR VASCULAR ASSESSMENT

(71) Applicant: CathWorks Ltd., Kfar Saba (IL)

(72) Inventors: Ifat Lavi, Moshav Mishmeret (IL); Guy Lavi, Moshav Mishmeret (IL)

(73) Assignee: CathWorks Ltd., Kfar Saba (IL)

( * ) Notice: Subject to any disclaimer, the term of this patent is extended or adjusted under 35 U.S.C. 154(b) by 0 days.

(21) Appl. No.: 16/538,579

(22) Filed: Aug. 12, 2019

(65) Prior Publication Data
US 2019/0365246 A1  Dec. 5, 2019

Related U.S. Application Data

(63) Continuation of application No. 15/910,900, filed on Mar. 2, 2018, now Pat. No. 10,376,165, which is a
(Continued)

(51) Int. Cl.
*A61B 34/10* (2016.01)
*A61B 5/026* (2006.01)
(Continued)

(52) U.S. Cl.
CPC ............ *A61B 5/026* (2013.01); *A61B 5/0035* (2013.01); *A61B 5/02* (2013.01); *A61B 5/02007* (2013.01); *A61B 5/02152* (2013.01); *A61B 5/107* (2013.01); *A61B 5/489* (2013.01); *A61B 6/03* (2013.01); *A61B 6/466* (2013.01); *A61B 6/507* (2013.01); *A61B 8/466* (2013.01); *A61B 34/10* (2016.02); *G16H 30/40* (2018.01);
(Continued)

(58) Field of Classification Search
CPC .................. A61B 5/026; A61B 5/0035; A61B 5/02007; A61B 5/021; A61B 5/02028; A61B 3/1233; A61B 3/1241; A61B 34/10; A61B 34/25
See application file for complete search history.

(56) References Cited

U.S. PATENT DOCUMENTS 5,150,292 A  9/1992  Hoffmann et al.
5,638,823 A  6/1997  Akay et al.
(Continued)

FOREIGN PATENT DOCUMENTS

EP  2633815  9/2013
WO  2007/066249  6/2007
(Continued)

OTHER PUBLICATIONS

Extended European Search Report, dated Nov. 4, 2019, for European Application No. 17798881.3 filed on May 16, 2017.
(Continued)

*Primary Examiner* — Carol Wang
(74) *Attorney, Agent, or Firm* — K&L Gates LLP; Louis C. Cullman; Dennis A. Majewski

(57) ABSTRACT

Systems and methods are described for the compositing together of model-linked vascular data from a plurality of sources, including at least one 2-D angiography image, for display in a frame of reference of the at least one angiography image. In some embodiments, a linking model comprises a data structure configured to link locations of angiographic images to corresponding elements of non-image vascular parameter data. The linking data structure is traversed to obtain a mapping to the frame of reference of one or more of the angiographic images.

27 Claims, 12 Drawing Sheets

Related U.S. Application Data continuation of application No. PCT/IL2017/050543, filed on May 16, 2017.

(60) Provisional application No. 62/336,835, filed on May 16, 2016.

(51) Int. Cl.

| | |
|---|---|
| *A61B 6/03* | (2006.01) |
| *A61B 5/02* | (2006.01) |
| *A61B 5/107* | (2006.01) |
| *A61B 5/0215* | (2006.01) |
| *A61B 5/00* | (2006.01) |
| *A61B 6/00* | (2006.01) |
| *A61B 8/00* | (2006.01) |
| *G16H 50/50* | (2018.01) |
| *G16H 30/40* | (2018.01) |
| *A61B 5/0205* | (2006.01) |
| *A61B 8/06* | (2006.01) |
| *A61B 8/08* | (2006.01) |
| *A61B 8/12* | (2006.01) |
| *A61B 34/00* | (2016.01) |
| *A61B 5/021* | (2006.01) |
| *G16H 50/30* | (2018.01) |

(52) U.S. Cl.
CPC ............ *G16H 50/50* (2018.01); *A61B 5/0044* (2013.01); *A61B 5/0066* (2013.01); *A61B 5/0084* (2013.01); *A61B 5/021* (2013.01); *A61B 5/0205* (2013.01); *A61B 5/02028* (2013.01); *A61B 6/032* (2013.01); *A61B 6/037* (2013.01); *A61B 6/503* (2013.01); *A61B 6/504* (2013.01); *A61B 6/5217* (2013.01); *A61B 8/06* (2013.01); *A61B 8/0883* (2013.01); *A61B 8/12* (2013.01); *A61B 8/5223* (2013.01); *A61B 34/25* (2016.02); *A61B 2576/02* (2013.01); *G16H 50/30* (2018.01)

(56) References Cited

U.S. PATENT DOCUMENTS

| | | | |
|---|---|---|---|
| 6,047,080 | A | 4/2000 | Chen et al. |
| 6,236,878 | B1 | 5/2001 | Taylor et al. |
| 6,842,638 | B1 | 1/2005 | Suri et al. |
| 7,369,691 | B2 | 5/2008 | Kondo et al. |
| 7,657,299 | B2 | 2/2010 | Huizenga et al. |
| 7,693,315 | B2 | 4/2010 | Krishnan et al. |
| 7,738,626 | B2 | 6/2010 | Weese et al. |
| 8,090,164 | B2 | 1/2012 | Bullitt et al. |
| 8,298,147 | B2 | 10/2012 | Huennekens et al. |
| 8,311,748 | B2 | 11/2012 | Taylor et al. |
| 8,311,750 | B2 | 11/2012 | Taylor |
| 8,548,778 | B1 | 10/2013 | Hart et al. |
| 8,554,490 | B2 | 10/2013 | Tang et al. |
| 8,560,968 | B1 | 10/2013 | Nair |
| 8,771,195 | B2 | 7/2014 | Kim et al. |
| 8,812,246 | B2 | 8/2014 | Taylor |
| 9,042,613 | B2 | 5/2015 | Spilker et al. |
| 9,078,564 | B2 | 7/2015 | Taylor |
| 9,189,600 | B2 | 11/2015 | Spilker et al. |
| 9,314,584 | B1 | 4/2016 | Riley et al. |
| 9,615,755 | B2 | 4/2017 | Riley et al. |
| 9,754,082 | B2 | 9/2017 | Taylor et al. |
| 9,814,433 | B2 | 11/2017 | Benishti et al. |
| 9,858,387 | B2 | 1/2018 | Lavi et al. |
| 10,342,442 | B2 | 7/2019 | Hattangadi et al. |
| 10,376,165 | B2 | 8/2019 | Lavi et al. |
| 10,470,730 | B2 | 11/2019 | Benishti et al. |
| 2003/0105401 | A1 | 6/2003 | Jago et al. |
| 2004/0019264 | A1 | 1/2004 | Suurmond et al. |
| 2004/0066958 | A1 | 4/2004 | Chen et al. |
| 2005/0043614 | A1 | 2/2005 | Huizenga et al. |
| 2007/0167833 | A1 | 7/2007 | Redel et al. |
| 2008/0020362 | A1 | 1/2008 | Cotin et al. |
| 2008/0205722 | A1 | 8/2008 | Schaefer et al. |
| 2009/0312648 | A1 | 12/2009 | Zhang et al. |
| 2010/0017171 | A1 | 1/2010 | Spilker et al. |
| 2010/0160764 | A1 | 6/2010 | Steinberg et al. |
| 2010/0220917 | A1 | 9/2010 | Steinberg et al. |
| 2010/0298719 | A1 | 11/2010 | Thrysoe et al. |
| 2011/0015530 | A1 | 1/2011 | Misawa |
| 2011/0096907 | A1 | 4/2011 | Mohamed |
| 2011/0142313 | A1 | 6/2011 | Pack et al. |
| 2011/0182492 | A1 | 7/2011 | Grass et al. |
| 2012/0041318 | A1 | 2/2012 | Taylor |
| 2012/0041739 | A1 | 2/2012 | Taylor |
| 2012/0053918 | A1 | 3/2012 | Taylor |
| 2012/0053921 | A1 | 3/2012 | Taylor |
| 2012/0059246 | A1 | 3/2012 | Taylor |
| 2012/0072190 | A1 | 3/2012 | Sharma et al. |
| 2012/0150048 | A1 | 6/2012 | Kang et al. |
| 2012/0177275 | A1 | 7/2012 | Suri |
| 2012/0230565 | A1 | 9/2012 | Steinberg |
| 2013/0060133 | A1 | 3/2013 | Kassab et al. |
| 2013/0094745 | A1 | 4/2013 | Sundar |
| 2013/0226003 | A1 | 8/2013 | Edic et al. |
| 2013/0324842 | A1 | 12/2013 | Mittal et al. |
| 2014/0094693 | A1 | 4/2014 | Cohen et al. |
| 2014/0100451 | A1 | 4/2014 | Tolkowsky et al. |
| 2014/0121513 | A1 | 5/2014 | Tolkowsky et al. |
| 2014/0303495 | A1 | 10/2014 | Fonte et al. |
| 2015/0201897 | A1 | 7/2015 | Kyriakou |
| 2015/0265162 | A1 | 9/2015 | Lavi et al. |
| 2015/0335304 | A1 | 11/2015 | Lavi et al. |
| 2015/0342551 | A1 | 12/2015 | Lavi et al. |
| 2016/0007945 | A1 | 1/2016 | Taylor |
| 2016/0110866 | A1 | 4/2016 | Taylor |
| 2016/0110867 | A1 | 4/2016 | Taylor |
| 2016/0128661 | A1 | 5/2016 | Taylor |
| 2016/0228000 | A1 | 8/2016 | Spaide |
| 2016/0247279 | A1 | 8/2016 | Lavi et al. |
| 2016/0371456 | A1 | 12/2016 | Taylor et al. |

FOREIGN PATENT DOCUMENTS

| | | |
|---|---|---|
| WO | 2010/033971 | 3/2010 |
| WO | 2014/064702 | 5/2014 |
| WO | 2014/111927 | 7/2014 |
| WO | 2014/111929 | 7/2014 |
| WO | 2014/111930 | 7/2014 |
| WO | 2015/059706 | 4/2015 |
| WO | 2017/199245 | 11/2017 |

OTHER PUBLICATIONS

Andriotis et al. "A New Method of Three-Dimensional Coronary Artery Reconstruction From X-Ray Angiography: Validation Against a Virtual Phantom and Multislice Computed Tomography", Catheterization and Cardiovascular Interventions, 71(1): 28-43, Jan. 1, 2008.

Applicant-Initiated Interview Summary dated Oct. 4, 2016 From the U.S. Appl. No. 14/040,688.

Applicant-Initiated Interview Summary dated Dec. 23, 2016 From the U.S. Appl. No. 14/761,079 (3 pages).

Barratt et al. "Reconstruction and Quantification of the Carotid Artery Bifurcation From 3-D Ultrasound Images", IEEE Transactions on Medical Imaging, XP011112233, 23(5): 567-583,May 1, 2004.

Bullitt et al. "Determining Malignancy of Brain Tumors by Analysis of Vessel Shape", Medical Image Computing and Computer-Assisted Intervention, MICCAI 2004 Conference Proceedings, Lecture Notes in Computer Science, LNCS, 3217:645-653, 2004.

Caiati et al. "New Noninvasive Method for Coronary Flow Reserve Assessment: Contrast-Enhanced Transthoracic Second Harmonic Echo Doppler", Circulation, 99: 771-778, 1999.

Caiati et al. "Detection, Location, and Severity Assessment of Left Anterior Descending Coronary Artery Stenoses by Means of Contrast-

(56) References Cited

OTHER PUBLICATIONS

Enhanced Transthoracic Harmonic Echo Doppler", European Heart Journal, 30: 1797-1806, 2009.
Communication Relating to the Results of the Partial International Search dated Feb. 6, 2015 From the International Searching Authority Re. Application No. PCT/IL2014/050923.
Communication Relating to the Results of the Partial International Search dated Jan. 30, 2014 From the International Searching Authority Re. Application No. PCT/IL2013/050869.
Communication Pursuant to Article 94(3) EPC dated Jul. 28, 2017 From the European Patent Office Re. Application No. 13796169.4. (8 Pages).
Communication Pursuant to Article 94(3) EPC dated Aug. 1, 2017 From the European Patent Office Re. Application No. 14710059.8. (7 Pages).
Communication Pursuant to Article 94(3) EPC dated Aug. 3, 2017 From the European Patent Office Re. Application No. 14708097.2. (7 Pages).
Frangi et al. "Multiscale Vessel and Enhancement Filtering", Medical Image Computing and Computer-Assisted Intervention, MICCA'98, Lecture Notes in Computer Science, 1496: 130-137, 1998.
Fusejima "Noninvasive Measurement of Coronary Artery Blood Flow Using Combined Two-Dimensional and Doppler Echocardiography", Journal of the American College of Cardiology, JACC, 10(5): 1024-1031, Nov. 1987.
Hawkes et al. "Validation of Volume Blood Flow Measurements Using Three-Dimensional Distance-Concentration Functions Derived From Digital X-Ray Angiograms", Investigative Radiology, 29(4): 434-442, Apr. 1994.
Hoffmann et al. "Determination of Instantaneous and Average Blood Flow Rates From Digital Angiograms of Vessel Phantoms Using Distance-Density Curves", Investigative Radiology, 26(3): 207-212, Mar. 1991.
Holdsworth et al. "Quantitative Angiographic Blood-Flow Measurement Using Pulsed Intra-Arterial Injection", Medical Physics, 26(10): 2168-2175, Oct. 1999.
Huo, Yunlong, and Ghassan S. Kassab. "Intraspecific scaling laws of vascular trees." Journal of The Royal Society Interface 9.66 (2012). pp. 190-200.
International Preliminary Report on Patentability dated Jul. 30, 2015 From the International Bureau of WIPO Re. Application No. PCT/IL2014/050044.
International Preliminary Report on Patentability dated May 6, 2016 From the International Bureau of WIPO Re. Application No. PCT/IL2014/050923.
International Preliminary Report on Patentability dated May 7, 2015 From the International Bureau of WIPO Re. Application No. PCT/IL2013/050869.
International Preliminary Report on Patentability dated Jul. 30, 2015 From the International Bureau of WIPO Re. Application No. PCT/IL2014/050039.
International Preliminary Report on Patentability dated Jul. 30, 2015 From the International Bureau of WIPO Re. Application No. PCT/IL2014/050043.
International Search Report and the Written Opinion dated Jul. 10, 2015 From the International Searching Authority Re. Application No. PCT/IL2014/050923.
International Search Report and the Written Opinion dated May 16, 2014 From the International Searching Authority Re. Application No. PCT/IL2014/050043.
International Search Report and the Written Opinion dated May 16, 2014 From the International Searching Authority Re. Application No. PCT/IL2014/050044.
International Search Report and the Written Opinion dated May 23, 2014 From the International Searching Authority Re. Application No. PCT/IL2013/050869.
International Search Report and the Written Opinion dated May 28, 2014 From the International Searching Authority Re. Application No. PCT/IL2014/050039.

Janssen et al. "New Approaches for the Assessment of Vessel Sizes in Quantitative (Cardio-) Vascular X-Ray Analysis", International Journal of Cardiovascular Imaging, 26: 259-271, 2010.
Kappetein et al. "Current Percutaneous Coronary Intervention and Coronary Artery Bypass Grafting Practices for Three-Vessel and Left Main Coronary Artery Disease. Insights From the SYNTAX Run-h1 Phase", European Journal of Cardio-Thoracic Surgery, 29: 486-491, Aug. 18, 2010.
Kirkeeide "Coronary Obstructions, Morphology and Physiologic Significance", Quantitative Coronary Arteriography, Chap. 11: 229-244, 1991.
Leonardou et al., "Close to transplant renal artery stenosis and percutaneous transluminal treatment." Journal of Transplantation (2011 ). pp. 1-8.
Lethen et al. "Validation of Noninvasive Assessment of Coronary Flow Velocity Reserve in the Right Coronary Artery. A Comparison of Transthoracic Echocardiographic Results With Intracoronary Doppler Flow Wire Measurements" European Heart Journal, 24: 1567-1575, 2003.
Meimoun et al. "Non-Invasive Assessment of Coronary Flow and Coronary Flow Reserve by Transthoracic Doppler Echocardiography: A Magic Tool for the Real World", European Journal of Echocardiography, 9: 449-457, 2008.
Mercer-Rosa et al., "Illustration of the additional value of real-time 3-dimensional echocardiography to conventional transthoracic and transesophageal 2-dimensional echocardiography in imaging muscular ventricular septal defects: Does this have any impact on individual patient treatment?" Journal of the American Society of Echocardiography 19.12 (2006): pp. 1511-1519.
Molloi et al., "Quantification of Fractional Flow Reserve Using Angiographic Image Data", World Congress on Medical Physics and Biomedical Engineering, Munich, Germany, Sep. 7-12, 2009, IFMBE Proceedings, 25/2: 901-904, 2009.
Molloi et al., Estimation of coronary artery hyperemic blood flow based on arterial lumen volume using angiographic images. Int. J. Cardiovasc. Imaging, 28(1):1-11 (2012).
Ng "Novel QCA Methodologies and Angiographic Scores", The International Journal of Cardiovascular Imaging, XP002718798, 27(2): 157-165, Feb. 20, 2011.
Notification of Office Action and Search Report dated Mar. 7, 2017 From the State Intellectual Property Office of the People's Republic of China Re. Application No. 201480014756.X. (6 Pages).
Official Action dated Aug. 15, 2016 From the U.S. Appl. No. 14/040,688.
Official Action dated Dec. 23, 2016 From the U.S. Appl. No. 14/437,205. 54 pages).
Official Action dated Dec. 24, 2015 From the U.S. Appl. No. 14/866,098.
International Search Report and the Written Opinion dated Aug. 24, 2017 From the International Searching Authority Re. Application No. PCT/IL2017/050543.
Official Action dated May 4, 2017 From the U.S. Appl. No. 14/761,079. (19 pages).
Official Action dated Nov. 7, 2016 From the U.S. Appl. No. 14/761,079. (37 pages).
Official Action dated Mar. 2, 2018 From the U.S. Appl. No. 14/761,064. (11 pages).
Pellot et al. "A 3D Reconstruction of Vascular Structures From Two X-Ray Angiograms Using an Adapted Simulated Annealing Algorithm", IEEE Transactions on Medical Imaging, 13(1): 48-60, Mar. 1994.
Pinho et al. "Assessment and Stenting of Tracheal Stenosis Using Deformable Shape Models", Medical Image Analysis, XP028364939, 15(2): 250-266, Dec. 2, 2010.
Sarwal et al., "3-D Reconstruction of Coronary Arteries." Proceedings of the 16th Annual International Conference of the IEEE Engineering in Medicine and Biology Society, Engineering Advances: New Opportunities for Biomedical Engineers, Nov. 3, 1994, pp. 504-505.
Seifalian et al. "A New Algorithm for Deriving Pulsatile Blood Flow Waveforms Tested Using Simulated Dynamic Angiographic Data", Neuroradiology, 31: 263-269, 1989.

(56) References Cited

OTHER PUBLICATIONS

Seifalian et al. "Blood Flow Measurements Using 3D Distance Concentration Functions Derived From Digital X-Ray Angiograms", Cardiovascular Imaging, Chap.33: 425-442, 1996.
Seifalian et al. "Validation of a Quantitative Radiographic Technique to Estimate Pulsatile Blood Flow Waveforms Using Digital Subtraction Angiographic Data", Journal of Biomedical Engineering, 13(3): 225-233, May 1991.
Shpilfoygel et al. "Comparison of Methods for Instantaneous Angiographic Blood Flow Measurement", Medical Physics, 26(6): 862-871, Jun. 1999.
Sianos et al., The SYNTAX Score: An Angiographic Tool Grading the Complexity of Coronary Artery Disease. EuroIntervention, XP055392801, 1(2):219-227, Aug. 2005.
Siogkas et al. "Quantification of the Effect of Percutaneous Coronary Angioplasty on A Stenosed Right Coronary Artery", 2010 10th IEEE International Conference on Information Technology and Applications in Biomedicine, ITAB 2010, Corfu, Greece, Nov. 3-5, 2010, p. 1-4, Nov. 2010. Abstract.
Slomka et al. "Fully Automated Wall Motion and Thickening Scoring System for Myocardial Perfusion SPECT: Method Development and Validation in Large Population", Journal of Nuclear Cardiology, XP002718797, 19(2): 291-302, Jan. 26, 2012.
Sprague et al. "Coronary X-Ray Angiographic Reconstruction and Image Orientation", Medical Physics, 33(3): 707-718, Mar. 2006.
Sun, Zhonghua, G. H. Choo, and K. H. Ng. "Coronary CT angiography: current status and continuing challenges." The British Journal of radiology 85.1013 (2012). pp. 495-510.
Takarada et al. "An Angiographic Technique for Coronary Fractional Flow Reserve Measurement: In Vivo Validation", International Journal of Cardiovascular Imaging, International Journal of Cardiovascular Imaging, Published Online, p. 1-10, Aug. 31, 2012.
Termeer et al. "Visualization of Myocardial Perfusion Derived From Coronary Anatomy", IEEE Transactions on Visualization and Computer Graphics, 14(6):1595-1602, Nov./Dec. 2008.
Third-Party Submission filed on Feb. 1, 2016 From the U.S. Appl. No. 14/040,688.
Third-Party Submission filed on Feb. 2, 2016 From the U.S. Appl. No. 14/437,205.
Third-Party Submission filed on Jun. 14, 2016 From the U.S. Appl. No. 14/437,205.
Third-Party Submission filed on Jan. 28, 2016 From the U.S. Appl. No. 14/761,064.
Third-Party Submission filed on Jan. 28, 2016 From the U.S. Appl. No. 14/761,086.
Third-Party Submission Under 37 CFR 1.290 Dated Oct. 19, 2015 From the U.S. Appl. No. 14/040,688.
Third-Party Submission Under 37 CFR 1.290 filed on Jun. 14, 2016 From the U.S. Appl. No. 14/761,064.
Third-Party Submission Under 37 CFR 1.290 filed on Jun. 14, 2016 From the U.S. Appl. No. 14/761,086.
Tomasello et al. "Quantitative Coronary Angiography in the Interventional Cardiology", Advances in the Diagnosis of Coronary Atherosclerosis, Chap. 14:255-272, Nov. 2011.
Translation of Notification of Office Action dated Mar. 7, 2017 From the State Intellectual Property Office of the People's Republic of China Re. Application No. 201480014756.X. (4 Pages).
Tu et al., Assessment of obstruction length and optimal viewing angle from biplane X-ray angiograms. Int. J. Cardiovasc. Imaging, 26:5-17 (2010).
Tu et al., In vivo assessment of optimal viewing angles from X-ray coronary angiography. EuroIntervention, 7:112-120 (2011).
Tu et al., The impact of acquisition angle differences on three-dimensional quantitative coronary angiography. Catheterization and Cardiovascular Interventions, 78(2):214-222 (2011).
Tu et al., In vivo assessment of bifucation optimal viewing angles and bifurcation angles by three-dimensional (3D) quantitative coronary angiography. Int. J. Cardiovasc. Imaging, (2011).
Tuinenburg et al. "Dedicated Bifurcation Analysis: Basic Principles", International Journal of Cardiovascular Imaging, 27: 167-174,2011.
USPTO Communication dated Feb. 8, 2016 Re Third-Party Submission From the US Patent and Trademark Office Re. U.S. Appl. No. 14/761,064.
USPTO Communication dated Feb. 8, 2016 RE Third-Party Submission From the US Patent and Trademark Office Re. U.S. Appl. No. 14/761,086.
USPTO Communication dated Feb. 9, 2016 Re Third-Party Submission From the US Patent and Trademark Office Re. U.S. Appl. No. 14/040,688.
USPTO Communication dated Feb. 19, 2016 Re Third-Party Submission From the US Patent and Trademark Office Re. U.S. Appl. No. 14/437,205.
USPTO Communication dated Jun. 22, 2016 Re Third-Party Submission From the US Patent and Trademark Office Re. U.S. Appl. No. 14/437,205.
USPTO Communication dated Jun. 22, 2016 Re Third-Party Submission From the US Patent and Trademark Office Re. U.S. Appl. No. 14/761,086.
USPTO Communication dated Jun. 22, 2016 Re Third-Party Submission From the US Patent and Trademark Office Re. U.S. Appl. No. 14/7761,064.
Voci et al. "Coronary Flow: A New Asset for the Echo Lab?", European Heart Journal, 25: 1867-1879,2004.
Weickert "Anisotropic Diffusion in Image Processing", ECMI, Published by Teubner, Stuttgart, Germany, 184 P., 2008.
Weickert et al. "A Scheme for Coherence-Enhancing Diffusion Filtering With Optimized Rotation Invariance", Computer Vision, Graphics, and Pattern Recognition Group, CVGPR Group, Technical Report, Computer Science Series, Apr. 2000: Feb. 1-20, 2000.
Weickert et al. "A Scheme for Coherence-Enhancing Diffusion Filtering With Optimized Rotation Invariance", Journal of Visual Communication and Image Representation, 13(1-2): 103-118, Mar. 2002. & Computer Vision, Graphics, and Pattern Recognition Group, CVGPR, Computer Science Series, Technical Report Apr. 2000, Feb. 2000.
Wong et al. "Quantification of Fractional Flow Reserve Based on Angiographic Image Data", International Journal of Cardiovascular Imaging, XP0350 12993, 28(1): 13-22, Published Online Jan. 7, 2011. Abstract, Section Angiographic BasedFFR'.
Wong et al. "Determination of Fractional Flow Reserve (FFR) Based on Scaling Laws: A Simulation Study", Physics in Medicine and Biology, 53: 3995-4011, 2008.
Wong et al., Automated technique for angiographic determination of coronary blood flow and lumen volume. Acad. Radiol., 13:186-194 (2006).
Yang et al. "Novel Approach for 3-D Reconstruction of Coronary Arteries From Two Uncalibrated Angiographic Images." IEEE Transactions on Image Processing, vol. 18, No. 7, Jul. 2009, pp. 1563-1572.
Youssef et al., "Role of Computed Tomography Coronary Angiography in the Detection of Vulnerable Plaque, Where Does It Stand Among Others?", Angiology, 1(2): 1000111-1- 1000111-8, 2013.
Zhang et al., Quantification of coronary microvascular resistance using angiographic images for volumetric blood flow measurement: in vivo validation. Am. J. Physiol. Heart Circ. Physiol., 300(6):H2096-H2104 (2011).

SYSTEM FOR VASCULAR ASSESSMENT

PRIORITY CLAIM

This application claims priority to and the benefit as a continuation of U.S. patent application Ser. No. 15/910,900, filed on Mar. 2, 2018, now U.S. Pat. No. 10,376,165, which is a continuation of International Application No. PCT/IL2017/050543, filed on May 16, 2017, which claims priority to U.S. Provisional Patent Application No. 62/336,835, filed May 16, 2016, the entire contents of each of which are incorporated herein by reference and relied upon.

TECHNICAL FIELD

The present disclosure relates to the field of medical image analysis, and more particularly, to the presentation of medical images of a vasculature.

BACKGROUND

Arterial stenosis is one of the most serious forms of arterial disease. In clinical practice, stenosis severity is estimated by using either simple geometrical parameters, such as determining the percent diameter of a stenosis, or by measuring hemodynamically based parameters, such as the pressure-based myocardial Fractional Flow Reserve (FFR). FFR is an invasive measurement of the functional significance of coronary stenoses. The FFR measurement represents a ratio between maximal blood flow in an area of stenosis and maximal blood flow in the same area without the stenosis. Earlier studies have shown that lesions with an FFR that is less than 0.75 provide an accurate predictor of ischemia; and that deferral of percutaneous coronary intervention for lesions with FFR≥0.75 appeared to be safe.

Modeling vascular flow to assess vascular flow is described, for example, in U.S. published patent application number 2012/0059246 of Taylor, to a "Method And System For Patient-Specific Modeling Of Blood Flow", which describes embodiments which include a system for determining cardiovascular information for a patient. The system may include at least one computer system configured to receive patient-specific data regarding a geometry of at least a portion of an anatomical structure of the patient. The portion of the anatomical structure may include at least a portion of the patient's aorta and at least a portion of a plurality of coronary arteries emanating from the portion of the aorta. The at least one computer system may also be configured to create a three-dimensional model representing the portion of the anatomical structure based on the patient-specific data, create a physics-based model relating to a blood flow characteristic within the portion of the anatomical structure, and determine a fractional flow reserve within the portion of the anatomical structure based on the three-dimensional model and the physics-based model.

Additional background art includes: U.S. Pat. No. 8,548,778 of Taylor.

Further background art includes U.S. Patent Publication No. 2015/0342551 to Lavi et al.; International Patent Publication No. WO2015/059706 to Lavi et al.; U.S. Patent Publication No. 2015/0335304 to Ifat Lavi et al.; U.S. Patent Publication No. 2015/0339847 to BenIshti et al.; and U.S. Patent Publication No. 2015/0265162 to Lavi et al.; the contents of which are hereby incorporated herein by reference.

SUMMARY

There is provided, in accordance with some exemplary embodiments, a method of preparing vascular parameter data for display. The example method includes receiving at least a first and a second 2-D angiographic image each comprising respective 2-D frames of reference and vascular image contents viewed from angles at least 30° different from each other. The example method also includes creating a model including a data structure configured to link a plurality of 2-D locations in each of the first and the second 2-D angiographic images and forming an image in the frame of reference of the first 2-D angiographic image. The example method further includes determining the vascular parameter data for the linked plurality of 2-D locations using the second 2-D angiographic image and displaying the vascular parameter data at the plurality of linked 2-D locations in the frame of reference of the first image.

According to some embodiments, display away from the linked 2-D locations is based on the first image.

According to some embodiments, the linking comprises association in common to an identifying tag.

According to some embodiments, the linking comprises association in common within a list.

According to some embodiments, the list is an ordered list.

According to some embodiments, the association in common is defined as position specified relative to other locations or elements of the ordered list.

According to some embodiments, display at the plurality of linked 2-D locations comprises a path rendered between some of the linked 2-D locations; the path being rendered to widths based on values derived from the processing of vascular widths in the correspondingly linked 2-D locations of the second image.

According to some embodiments, the width is rendered to at least 1.5× greater scale than the scale of the vascular diameter in the frame of reference of the first image.

According to some embodiments, display at the linked 2-D locations comprises a path rendered between linked 2-D locations, the path having a color assigned based on values of the accessed vascular parameter data.

According to some embodiments, display at the linked 2-D locations comprises a path rendered between linked 2-D locations, the path having at least one of a transparency or a gap assigned based on values of the accessed vascular parameter data.

According to some embodiments, display at each of the linked 2-D locations is based on a plurality of accessed parameter data elements.

According to some embodiments, the data structure links at least a third 2-D angiographic image not registrable to consistently align with the first and second images by an invertible 2-D geometrical transform, and at least some values of the accessed vascular parameter data elements are derived from processing of the correspondingly linked 2-D locations of the third image.

According to some embodiments, the display at the plurality of linked 2-D locations comprises display using any combination of displayed path width, display color, display transparency, or display color channel assignment.

According to some embodiments, the plurality of accessed parameter data elements represent the same vascular parameter for a plurality of parameter values.

According to some embodiments, the plurality of parameter values comprise values representing the vasculature in different states.

According to some embodiments, display at each of the linked 2-D locations alternates between being based on different element accessed vascular parameter data.

According to some embodiments, the image contents of at least the first and second images comprise views of a vasculature taken from different view angles.

According to some embodiments, the image contents of at least the first and second images comprise views of a vasculature in at least two respective different anatomical states.

There is provided, in accordance with some exemplary embodiments, a system for preparing vascular parameter data for display comprising: a processor configured to traverse a linkage model stored in digital memory, the linkage model comprising: at least a first and a second 2-D angiographic image representing respectively at least two separate viewing angles of a cardiac vasculature, and a data structure linking corresponding 2-D locations of the 2-D angiographic images, the corresponding comprising representation in common of a region of the cardiac vasculature; wherein the processor is furthermore configured to form for display a display image in the frame of reference of the first image; and wherein the display image at the plurality of linked 2-D locations in the frame of reference of the first image is based on at least vascular parameter data accessed by use of the linking data structure; and wherein the accessed vascular parameter data is derived from processing of the correspondingly linked 2-D locations of the second image.

According to some embodiments, the display image away from the linked 2-D locations is based on the first image.

According to some embodiments, the linking comprises association in common to an identifying tag.

According to some embodiments, the linking comprises association in common within a list.

Unless otherwise defined, all technical and/or scientific terms used herein have the same meaning as commonly understood by one of ordinary skill in the art to which the disclosure pertains. Although systems, methods, and/or computer program products similar or equivalent to those described herein can be used in the practice or testing of embodiments disclosed herein, exemplary systems, methods, and/or computer program products are described below. In case of conflict, the patent specification, including definitions, will control. In addition, the systems, methods, computer program products, and examples are illustrative only and are not intended to be necessarily limiting.

As will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.), or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments disclosed herein can involve performing and/or completing selected tasks manually, automatically, or a combination thereof. Moreover, according to actual instrumentation and equipment of some embodiments of the method and/or system disclosed herein, several selected tasks could be implemented by hardware, by software or by firmware and/or by a combination thereof, e.g., using an operating system.

For example, hardware for performing selected tasks according to some embodiments of the disclosure could be implemented as a chip or a circuit. As software, selected tasks according to some embodiments of the disclosure could be implemented as a plurality of software instructions executed by a computer using any suitable operating system. In an exemplary embodiment of the disclosure, one or more tasks, according to some exemplary embodiments of a method and/or a system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection may be provided. A display and/or a user input device such as a keyboard or mouse may also be provided.

Any combination of one or more computer readable medium(s) may be utilized for some embodiments of the disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Additional features and advantages of the disclosed system, method, and apparatus are described in, and will be apparent from, the following Detailed Description and the Figures.

BRIEF DESCRIPTION OF THE DRAWINGS

Some embodiments of the example systems, methods, and/or computer program products are herein described, by way of example only, with reference to the accompanying drawings. With specific reference now to the drawings in detail, it is stressed that the particulars shown are by way of example, and for purposes of illustrative discussion of embodiments disclosed herein. In this regard, the description taken with the drawings makes apparent to those skilled in the art how embodiments of the disclosure may be practiced.

In the drawings.

DETAILED DESCRIPTION

Figure 1A:
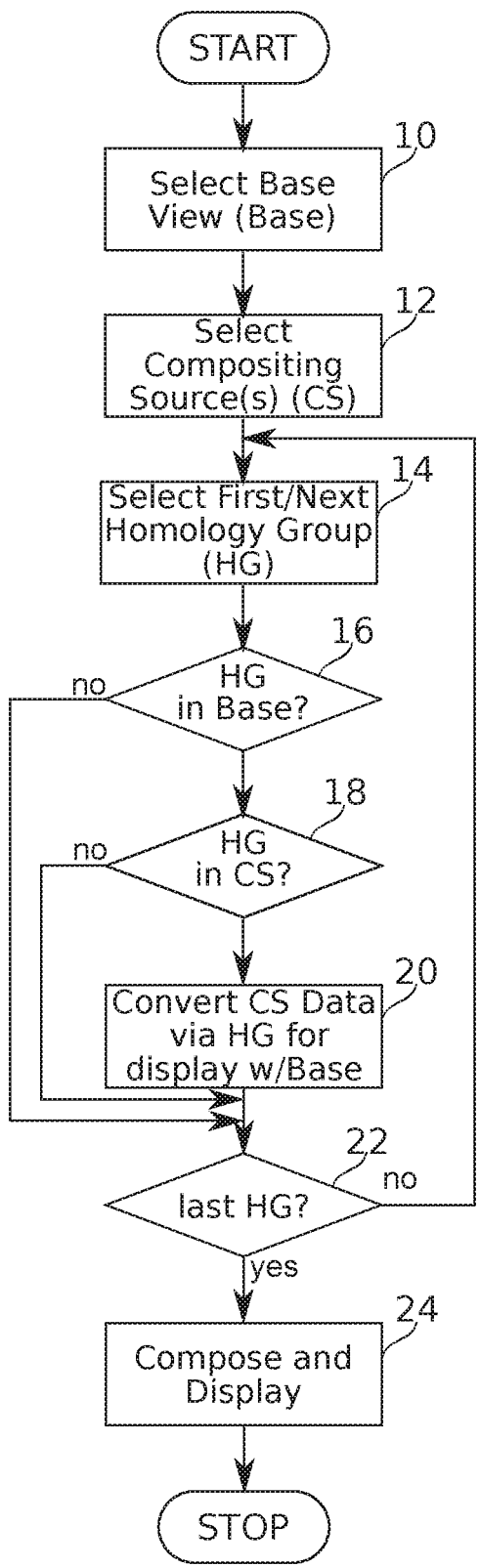
FIG. 1A is a schematic flowchart providing for a construction of an overlaid and/or composited display of vascular image and/or other vascular data, according to some embodiments of the present disclosure.

The present disclosure, in some embodiments thereof, relates to the field of medical image analysis, and more particularly, to the presentation of medical images of a vasculature.

Overview

An aspect of some embodiments of the current disclosure relates to the compositing together of model-linked vascular data from a plurality of sources, including, for example, at least one 2-D angiography image, for display in the frame of reference of the at least one angiography image.

In some embodiments, model linking of vascular data comprises a plurality of 2-D angiographic images, along with additional vascular parameter data. Optionally, at least some of the additional vascular parameter data is derived from analysis of the 2-D angiographic images. Additionally or alternatively, at least some of the additional vascular parameter data is derived from another source; for example, another imaging modality, and/or another sensing modality such as sensing from a catheter probe. In some embodiments, the 2-D angiographic images are taken from significantly different view angles (for example, from view angles different by at least 15°, 30°, 45°, 60°, 90°, 135°, or 180°). The different view angles potentially interfere with direct registration of the images based on correlations among their visual features. This is potentially of particular relevance for a vasculature such as the coronary vasculature, in which a single 2-D image compresses depth information around the curvature of the heart. In some embodiments, the 2-D angiographic images comprise images taken of a vascular anatomy in different states—for example, different states of disease progression and/or treatment—and/or at different times, between which the anatomical structure of the vascular has changed.

In some embodiments, the model comprises a data structure linking corresponding regions of 2-D angiographic images and/or corresponding elements of non-image vascular parameter data. The linkage is made between data samples which represent in common a region of the cardiac vasculature. For example, linkage is between data samples which represent features and/or characteristics of a particular part of a particular vascular segment. In some embodiments, parameter data which is sparsely available for the imaged vasculature is linked to a particular segment or other vascular domain that encompasses a plurality of linkage regions.

Optionally, the linkage regions defined are fully isomorphic with anatomy (e.g., linkage is based on representation of the same vascular tissue). This is a potential advantage when images in a model are of the same vasculature acquired at substantially the same time (e.g., without anatomical remodeling between their times of acquisition). Optionally or additionally, the linking region is relative to some other definition; for example, a region of a vasculature that is 10% of a total distance between two vascular branch points. This is potentially advantageous when linking between images which represent different anatomical states (for example, images taken during the course of a disease which comprises changes in vascular shapes, plaque development, or other anatomical changes). In the memory of a computerized implementation of the example model, linkage optionally has one of several forms; for example; common reference to an identifier or other token, common relative and/or absolute position within a data structure (optionally corresponding, for example, to relative distance along a vascular centerline), and/or common presence (optionally, presence by reference) in a row, column, or other compartment of a data structure.

In a 2-D image, optionally, only a portion of the image regions is linked into the linkage model. For example, in some embodiments, only vascular regions are linked to the linkage model. In some embodiments, vascular centerlines are linked to the linkage model. Optionally, non-linked elements in an image are connected to the linked model indirectly through their relationship (e.g., their relationship in the coordinate system of the 2-D image) to elements that are so-linked.

In some embodiments of the disclosure provided herein, creation of a composited image for display comprises traversing the model between two or more data sources (e.g., two or more images, an image and model-mapped non-image data, or another combination), based on their common linkage. It should be understood that in some embodiments, the linkage is not itself inherently geometrical and/or spatial in nature. For example, the linkage is optionally not biject (one-to-one between linked elements), and optionally comprises a linkage to a data set, which is not itself geometrically specified. Optionally, however, the linkages themselves are associated with information that is topographical (e.g., reflects anatomical connectivity) and/or is ordered (e.g., there is an ordering of links in a list, such as an order corresponding to relative position along a longitudinal extent of a vascular segment).

In some embodiments, individual 2-D images comprise at least a 2-D frame of reference. Optionally, the 2-D frame of reference is also associated with a 3-D frame of reference, for example, an image plane, a bounding box, a set of rays in 3-D space that intersect the image plane, or another 3-D plane of reference. Pixels or other elements (e.g. vascular centerlines) of or derived from the 2-D images optionally are assigned coordinates in the 2-D frame of reference. Optionally, the traversal of the model allows non-image data and/or other-image data to be "imported" to the 2-D coordinate system according to its linkage in the model to a region of the 2-D image that has such assigned coordinates. At least insofar as linkages are optionally not biject or between geometrically specified data sets, the importing transformation optionally does not comprise a geometrical transformation as such. In some embodiments, the individual 2-D images are sufficiently different from each other (for example, due to difference in view angle and/or changes in imaged anatomy which produce a different 3-D conformation of the vasculature) such that no invertible geometrical transform, also in two dimensions, can register them to each other. In some embodiments, a difference in view angle between at least one pair of vascular images having contents linked by the model is at least 15°, 30°, 45°, or another larger, smaller, or intermediate angle.

In some embodiments, a composited image comprises an image for computer-mediated display, which is based on at least a portion of a 2-D angiographic image and some other data from a source that is not originally and/or natively in the frame of reference of the 2-D angiographic image. In some embodiments, the composited image comprises a base image with one or more overlays (for example, overlays in a z-order, which may be understood as extending between a "top" and a "bottom" of a stack of layers, where each layer at least partially obscures underlying layers at regions where the upper layer is populated by display data). Optionally, overlays are at least partially transparent. In some embodiments, a composited image comprises images which are combined into a single layer, for example by use of image algebraic operations including but not limited to addition, subtraction, multiplication and/or division. Optionally, compositing comprises normalization and/or filtering of one or more composited images. Optionally, compositing comprises assignment of different display channels (e.g., color channels) to different data sources and/or different combinations thereof. Optionally, composited images are adjustable to show or hide different elements; e.g., by operation by a user of a user interface. In some embodiments, display of composited image elements is separated in time. For example, two composited layers are shown alternately, which potentially is useful for purposes of layer comparison.

Before explaining at least one embodiment of the disclosure in detail, it is to be understood that the example systems, methods, and/or computer program products provided herein are not necessarily limited in its application to the details of construction and the arrangement of the components and/or methods set forth in the following description and/or illustrated in the drawings. The example systems, methods, and/or computer program products are capable of embodying other embodiments or of being practiced or carried out in various ways.

Construction of Vascular Overlays and Composite Images Based on Correspondence Modeling of Vascular Data Reference is now made to FIG. 1A, which is a schematic flowchart of a construction of an overlaid and/or composited display of vascular image and/or other vascular data, according to some embodiments of the present disclosure. Reference is also made to FIG. 1D, which schematically presents a simplified correspondence model used in the construction, according to some embodiments of the present disclosure.

In some embodiments, a data display comprises a display of vascular parameter data within a coordinate frame determined by a base 2-D vascular image. Optionally, the display of vascular parameter data is overlaid on the 2-D vascular image. Additionally or alternatively, in some embodiments, a data display comprises a display composited (e.g., by use of arithmetic image operations and/or color and/or transparency channel recoding of images) from a plurality of 2-D vascular images, transformed to the coordinate frame of the base 2-D vascular image.

In some embodiments, the base 2-D vascular image, which provides the coordinate frame, comprises image data obtained, for example, by X-ray angiography, and/or from angiographic computed tomography (CT), magnetic resonance imaging (MRI), positron emission tomography (PET), optical coherence tomography (OCT), and/or intravascular ultrasound (IVUS). Vascular parameter data optionally comprises, for example, values of vascular width, curvature, digital FFR, blood pressure, and/or another parameter. Optionally, parameter values are continuously or sparsely specified along the length of vascular segments, and/or specified as values pertaining to particular vascular segment lengths.

In some embodiments, the vascular parameter data is matched to display coordinates taken from the 2-D vascular image via a correspondence model. The correspondence model comprises links between data in different images and/or data modalities, by specifying which data associated with the same anatomical location are indexable to one another. Optionally, data are associated in such a way that there is no canonical (that is, no single governing) spatial and/or planar location assigned to an anatomical location. Rather, there is optionally different positional information associated with the anatomical information for each of a plurality of different data sets within which the anatomical location is represented. Except for the correspondence relationship established within the model, there is no general requirement that the positional information of one data set should be consistent in space with the positional information in any other data set.

An example model 50 (FIG. 1D) is now described as a schematic example of correspondence, and/or of its potential advantages. A model that optionally comprises additional features is described, for example, in relation to FIG. 2B. The image data related to each other by the model 50 comprise at least a first angiographic image 52 and a second angiographic image 54. In some embodiments, centerline positions along blood vessel images 51, 53 (arranged, for example, as arrays or as another collection structure) are part of the model 50; defined for each of the images 52, 54. It should be understood that vascular centerline position is used herein for purposes of illustration, and is not limiting. However, use of 2-D image centerline position has the potential advantage of being readily calculated from a 2-D image, while compactly identifying locations distributed along a vascular extent.

The example model 50 links each set of centerline positions of blood vessel images 51, 53 (which may be an image pixel coordinate, for example) to one of a plurality of identifiers 56. The linkage is such that there are identifiers 56 linked to a centerline position (e.g., positions 51A, 53A) in each of the first angiographic image 52, and the second angiographic image 54. Moreover, when the position-to-identifier linkages are established, care is taken that positions linked to the same identifier also image substantially the same anatomical position. Methods for doing this include, for example, directly identifying homologies between the 2-D images, and/or techniques for back-projecting rays from 2-D images taken from different angles to their region of closest intersection. Such methods have been described, for example, in International Patent Publication No. WO2014/111930 to the Applicant, filed Jan. 15, 2014, the contents of which are incorporated by reference herein in their entirety.

For vascular targets in particular, such techniques permit identification of substantially identical anatomical positions in 2-D images even though they may be very different in the views they capture. It should be understood that the identifiers 56 can be established in one of several forms. In some embodiments identifiers comprise tags and/or indices. Optionally, tags and/or indices are defined to have some kind of ordered relationship, for example, an ordered relationship based on position along a vascular segment, and/or branch position within a tree of vascular segments. In some embodiments, identifiers are established as positions along a non-spatial frame of reference. An example of this is a vascular tree organized as branch nodes and distances (optionally, relative distances) along vascular segments joining the nodes.

Moreover, identifiers are optionally defined at one or more levels of specification. For example, all data pertaining to a particular vascular segment optionally share an identifier for that segment. Within the segment, data are optionally further identified by one or more position identifiers (e.g., distance along the segment and/or index into a position-ordered array of sub-segment identifiers).

Herein, the term "homology group" is used to refer to the set of all data which share linkage to a certain identifier, whether it is a high-level identifier (such as a segment identifier), or a low-level identifier (such as a sub-segment position identifier). Those data are said to be members of the same homology group, and/or said to share their anatomical identification. Conversely, herein, a homology group is said to be "in" (or "represented in") a certain data set (such as an image) if any member or region of the data set is a member of the homology group.

From the foregoing, it may be understood how a model can define common anatomical locations for different regions of different images, without requiring a common spatial frame of reference. For example, there is no inherent dominance between the coordinate frames of the first and second angiographic images 52, 54. There is not even a requirement that the coordinate frames of the two images be uniquely localized within a mutual (e.g., 3-D) frame of reference. In some embodiments, it is potentially infeasible to identify such a coordinate frame. For example, there may be only an approximate consensus available. Reasons for this include the potential for unknown relative errors in determining the positions of all relevant components of the imaging system, movements during imaging, and/or changes in some details of the anatomy itself over time. Any of these could introduce inconsistencies between images in a data set which are difficult to entirely eliminate.

It is noted, moreover, that a data set need not comprise image data in order to be integrated with model 50. Other data 58 optionally comprises, for example, non-image data such as values of vascular width, curvature, digital FFR, blood pressure, and/or another parameter, each value being linked to one or more homology groups. In some examples, the other data 58 may include a measurement related to the entire vascular structure, such as blood pressure. In these examples, the other data 58 is associated with substantially all of the identifiers 56. In other examples, the other data 58 may be obtained from intravenous measurements (e.g., FFR, blood pressure, etc.) at specific points in the blood vessels shown in images 51, 53. In these other examples, a user may select the appropriate identifier(s) 56 based on location(s) of the measurement(s). In other instances, measurement tools may determine a location of the measurement or provide the measurement in conjunction with an image. The other data 58 in these other instances is assigned to the appropriate identifier 56 based on the identified location provided in the data and/or through image analysis/correlation with model 50 and/or images 52, 54.

The other data 58 may also be determined from the images 52, 54, and/or other images. For example, values of vascular width, curvature, and/or diameter may be determined from the images 52, 54, and/or other images. The locations from where the values are determined are correlated to the model 50 and/or the images 52, 54 and associated with the appropriate identifier(s) 56.

Lack of dependency on a unique spatial frame of reference is a potential advantage for the modeling of cardiac vasculature in particular, where heartbeat and respiratory movement is continuous. It can also be a potential advantage for the representation of disease progression in which anatomical details (e.g. sizes, spatial positions, tortuosities, and/or degrees of occlusion) can change over time so that no single spatial representation can include all available data. Moreover, vascular images are often captured under conditions of limited signal-to-noise, and may be prone to other imperfections. Interpretation can depend on subtleties of shape or intensity which might be lost or distorted upon transforming an image into a new frame of reference. Thus, it is a potential advantage for a vascular model to be well-integrated with the presentation of original image data, which some embodiments of correspondence-based modeling allow.

Nevertheless, it is also a potential advantage to be able to rapidly prepare results from a plurality of data sources having disparate positional definitions for viewing within a common frame of reference. In some embodiments, a correspondence model is used to achieve this, optionally in real time.

A method of compositing image and measurement data (for example) for display is described below. It should be understood that the order of individual operations shown is illustrative, and may be performed in a different order (for example, composition to an image described in relation to block 24 is optionally performed along with the position-mapping operations of block 20), in concerted form (for example, the tests of block 16 and 18 are optionally comprised within the selection of block 14), and/or otherwise suitably rearranged from the order presented herein.

At block 10, in some embodiments, a base view is selected. The base view comprises a visual display coordinate system together with data indexed to that display coordinate system—typically, an image. In some embodiments, the base view comprises an originally acquired 2-D angiographic image 52. At least some coordinates in the base view are linked to the vascular model 50, for example, via identifiers 56.

At block 12, in some embodiments, one or more compositing data sources are selected. Compositing data sources optionally correspond to "other data" 58 as described in relation to FIG. 1D. The compositing data sources comprise, for example, measurements of vascular parameters such as width, diameter or radius (simulated or actual); FFR (fractional flow resistance)—invasively determined, image-based calculated, and/or simulated; curvature and/or tortuosity; plaque burden and/or calcification; relative flow and/or flow velocity; pressure and/or pressure change; TIMI (thrombolysis in myocardial infarction) grade and/or frame count; simulated stent; perfusion and/or tissue territory information (e.g., from MIR, CT, PET, and/or SPECT); one or more SYNTAX SCORE sub-scores; and/or vascular deformation information, for example as derived from a cine sequence of angiographic images.

In some embodiments, compositing data sources comprise additional image information. For example, a compositing data source may include an image taken before or after the image forming the base references frame. This is of potential benefit, for example, to allow the visualization of changes in vascular collateral structure, changes in vascular width due to disease progression, and/or changes in vascular width as a result of a treatment (such as a stent placement).

Data in the one or more compositing data sources are linked to the vascular model 50 via identifiers 56.

At block 14, in some embodiments, a first homology group is selected for processing into a composited view. The homology group is optionally comprised of one or more identifiers from identifiers 56.

At block 16, in some embodiments, a determination is made as to whether the selected homology group is in the base view. If it is not, (e.g., there is no place for compositing data linked to the homology group to be displayed), flow continues with block 22.

At block 18, in some embodiments, a determination is made as to whether the selected homology group is at least one of the compositing sources. If it is not, (e.g., there is no compositing data linked to the homology group to be displayed), flow continues with block 22.

At block 20, in some embodiments, compositing source data is associated to one or more positions in the coordinate system of the base view via links made through the homology group. Details of a method of performing block 20 are described, for example, in relation to FIG. 1B.

At block 22, in some embodiments, if the last homology group has been processed, the flowchart continues with block 24. Otherwise, the flowchart returns to block 14.

At block 24, in some embodiments, compositing comprises conversion of an image of the base view with the mapped data of the compositing source(s). Optionally, the compositing comprises any method for compositing two images together; for example, opaque and/or transparent overlay, assignment of composited parts to separate color channels, and/or arithmetical operations.

Figure 1B:
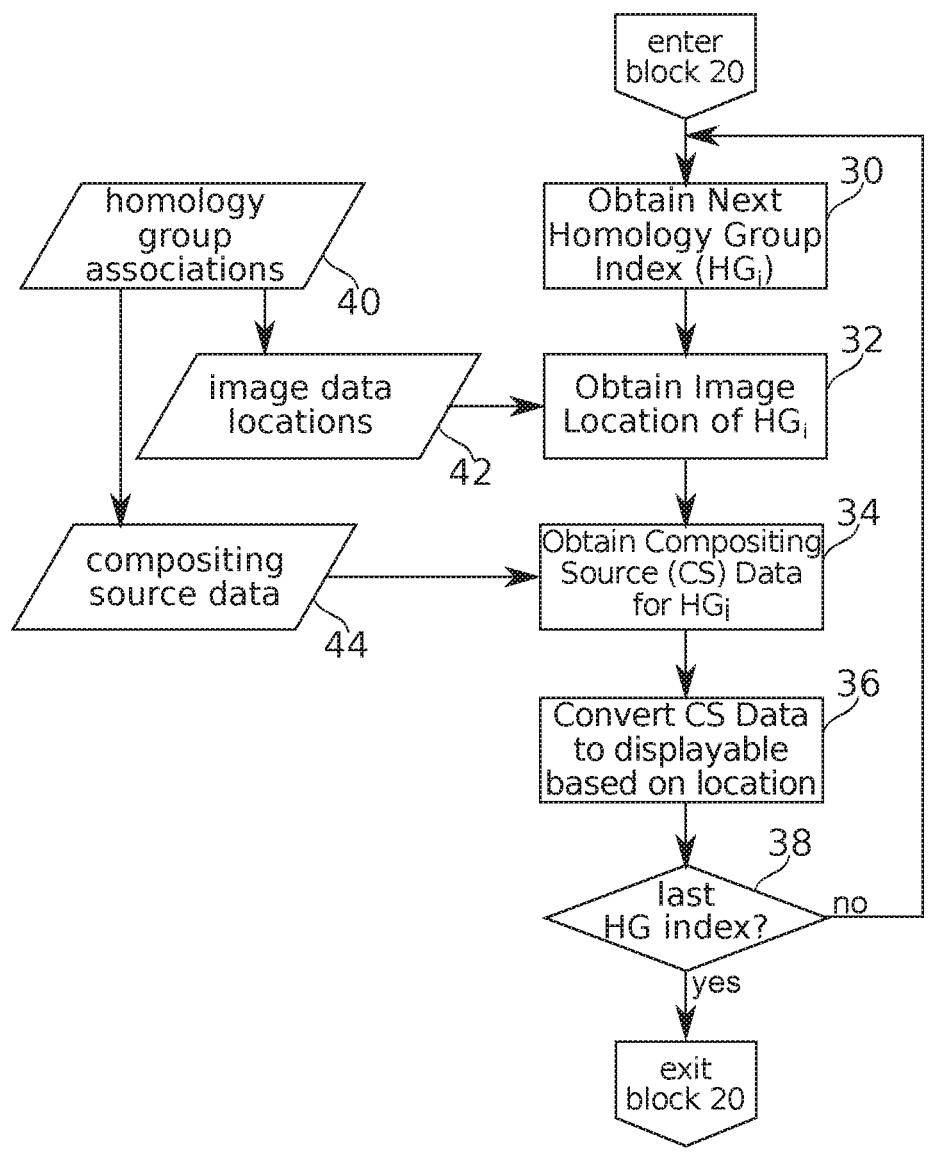
FIG. 1B is a schematic flowchart for the conversion of compositing source data to a form displayable as an image together with corresponding image data, according to some embodiments of the present disclosure.

Reference is now made to FIG. 1B, which is a schematic flowchart for the conversion of compositing source data to a form displayable as an image together with corresponding image data, according to some embodiments of the present disclosure. In some embodiments, the operations of FIG. 1B comprise sub-operations of block 20 of FIG. 1A. The flowchart of FIG. 1B illustrates a single compositing source 44, however, it should be understood that it can be applied to any number of compositing sources.

At block 30, in some embodiments, the flowchart begins, and the next index within the currently selected homology group is obtained. Optionally, e.g., for a homology group such as a vascular branch and/or vascular segment, and a data source that is described as function of position along the branch, the index is to a region along the length of the vascular branch. Optionally, e.g., if the data source comprises one value for the current homology group, there is only one index.

At block 32, in some embodiments, an image location (on the base view) linked to the homology group index is obtained. In some embodiments, this is found by examining links between the homology group associations 40 (optionally corresponding to identifiers 56), and image data locations 42 (optionally corresponding, for example, to centerline positions 51, 53). The base view can represent any view scale and/or orientation (and in some preferred embodiments, any scale and/or orientation of the coordinate system of an original angiographic image).

At block 34, in some embodiments, the corresponding compositing source data for the selected homology group index is obtained. Once again, in some embodiments, this includes examining links between the homology group associations 40 and the compositing source data 44.

At block 36, in some embodiments, the obtained image location of block 32 is assigned to the obtained compositing source data of block 34. Optionally, this comprises, for example, assignment in a tabular data structure, placement of one or more pixels in an overlay (immediately and/or just before compositing), and/or construction of a drawing command (e.g., of a stream of drawing commands) or drawing object (e.g., an XML object of an XML-encoded drawing file).

It should be understood that the spatially (3-D) distributed regions of a vasculature, such as a cardiac vasculature, have no fixed position relationship relative to one another in an arbitrarily oriented 2-D angiographic image of the vasculature. Optionally, anatomical regions move through time as well, for example, as a function of respiratory and/or cardiac motion, and/or as a function of evolving actual and/or simulated disease state. Accordingly, in some embodiments, there is a plurality of potential base images, each having an equivalent relationship to the same compositing source data as far as spatial position is concerned. The compositing source data itself is optionally free of spatial position information, apart from its homology group links. Optionally, compositing source data can be composited to base views, which themselves are spatially incompatible with one another, since there is optionally no canonical view and/or anatomical state to which they preferably apply.

At block 38, in some embodiments, if there are more indices in the homology group to map, flow returns to block 30. Otherwise, the flowchart ends.

Example of a Graphical User Interface for Data Selection and Presentation

Figure 1C:
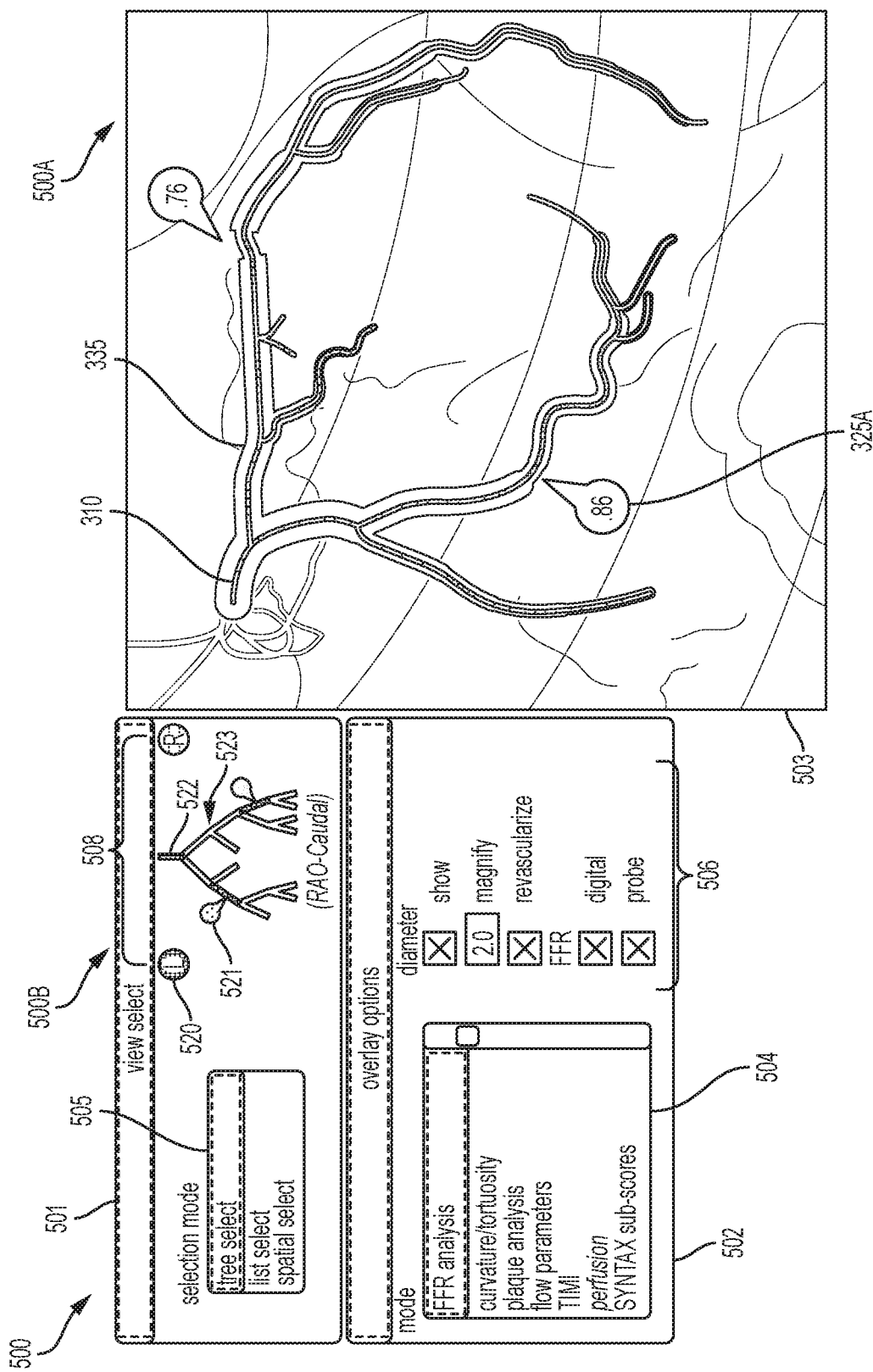
FIG. 1C schematically illustrates a graphical user interface according to some embodiments of the present disclosure.
Figure 1D:
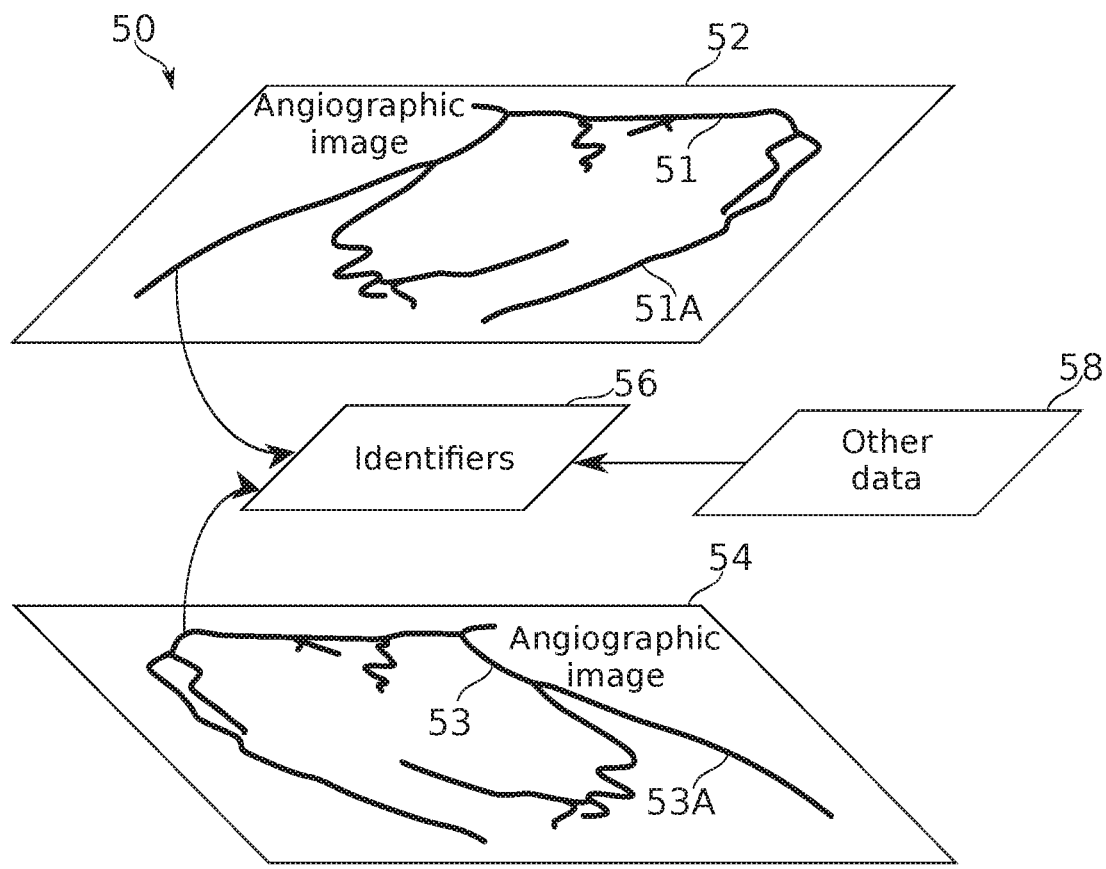
FIG. 1D schematically presents a simplified correspondence model used in the construction, according to some embodiments of the present disclosure.

Reference is now made to FIG. 1C, which schematically illustrates a graphical user interface 500 for interacting with an angiographic image, according to some embodiments of the present disclosure.

In some embodiments, the example graphical user interface 500 comprises an image display region 500A and optionally a control/indicator region 500B. Optionally, the two regions overlap, and/or are alternately or intermittently presented.

In some embodiments, image display region 500A comprises an angiographic image 503. Optionally, angiographic image 503 is presented as and/or together with one or more overlay and/or composited elements, for example, elements described in relation to FIGS. 3A-3J herein. FIG. 1C shows a region tag 325A, a shading-encoded (e.g., color-encoded) vascular tree 310, and a width encoded vascular tree 335.

Also shown are examples of an interface for view selection 501, including a mode selection menu 505, which optionally allows choosing a mode for selecting vascular segments and/or vascular segment regions. For example, the "tree select" mode interface 508 shown displays an abstracted model of a vascular tree 523 (connectivity is shown, but other geometry is suppressed). Optionally, view of the left or right coronary artery tree is selectable, for example, by a control such as radio buttons 520. Optionally, segments calculated to have particular clinical significance are indicated, for example, by callout tags 521, and/or by another indication. Optionally, the view angle of the image 503 shown in image display region 500A is selected based on segments of interest (e.g., darkened segments 522), which the user indicates (e.g., by clicking), and/or are selected by default according to which vascular segments appear to have the most clinical significance, e.g., due to a reduced vascular diameter. Optionally, a view angle is automatically selected as a view angle based on the selected segments of interest, and one or more criteria for their optimal display. The criteria for optimal display optionally comprise, for example, strong contrast along the vascular extent, and/or vascular extent which is the longest in the 2-D frame of reference that the image displays. It is to be understood that other modes of vascular segment selection are optionally provided, for example, from a list ("list select") and/or from a 3-D view of the vascular tree ("spatial select").

In some embodiments, an overlay option interface 502 provides for selection of one or more overlay options. FIG. 1C shows selection of an "FFR analysis" mode (fractional flow reserve analysis). In addition, FIG. 1C shows controls 506 that provide for selection of overlay options. Control of the vascular width display 335 comprises, for example, a control to show/hide the overlay component, a width magnification control (2× the actual proportional width is shown), and/or to show revascularized width at parts of the vascular tree which are determined by FFR analysis to be significantly stenotic. The "FFR" set of controls includes switches to turn on or off display of digital FFR (corresponding to shading-encoded tree 310), and/or probe-determined FFR value tags 325A.

It is to be understood that one or more additional overlay option modes are optionally provided; for example: for the display of such parameters as curvature, tortuosity, analysis of plaque positions and/or thickness, analysis of other flow parameters, TIMI grade, tissue perfusion analysis, and/or vascular state scoring such as SYNTAX Score and/or its subscores. Optionally, these correspond, for example, to any of the compositing data sources described in relation to block 12 of FIG. 1A.

Correspondence Modeling of a Vasculature

Figure 2A:
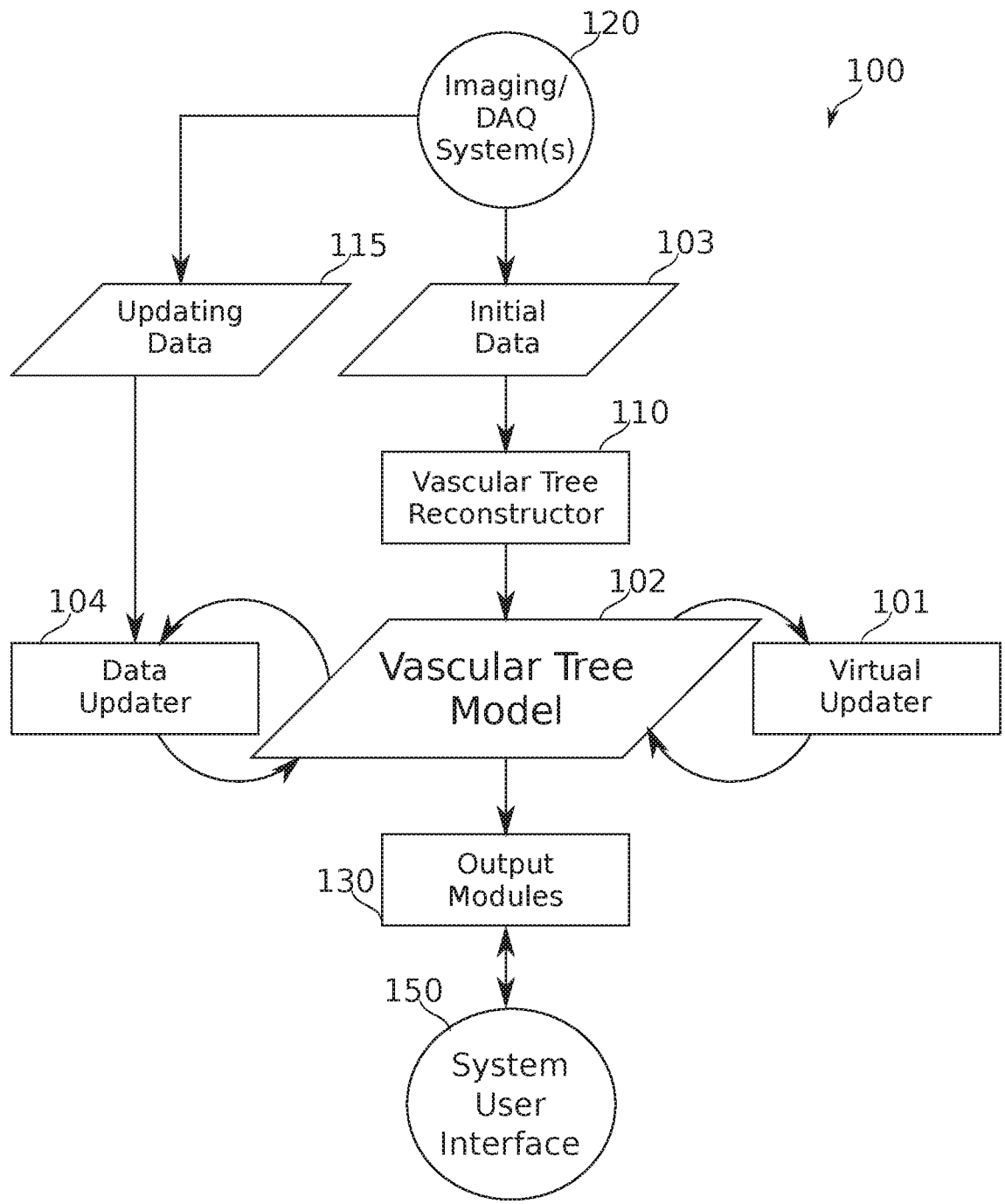
FIG. 2A is a block diagram of a system for production and use of a dynamically updatable vascular tree model, according to some exemplary embodiments of the present disclosure.
Figure 2B:
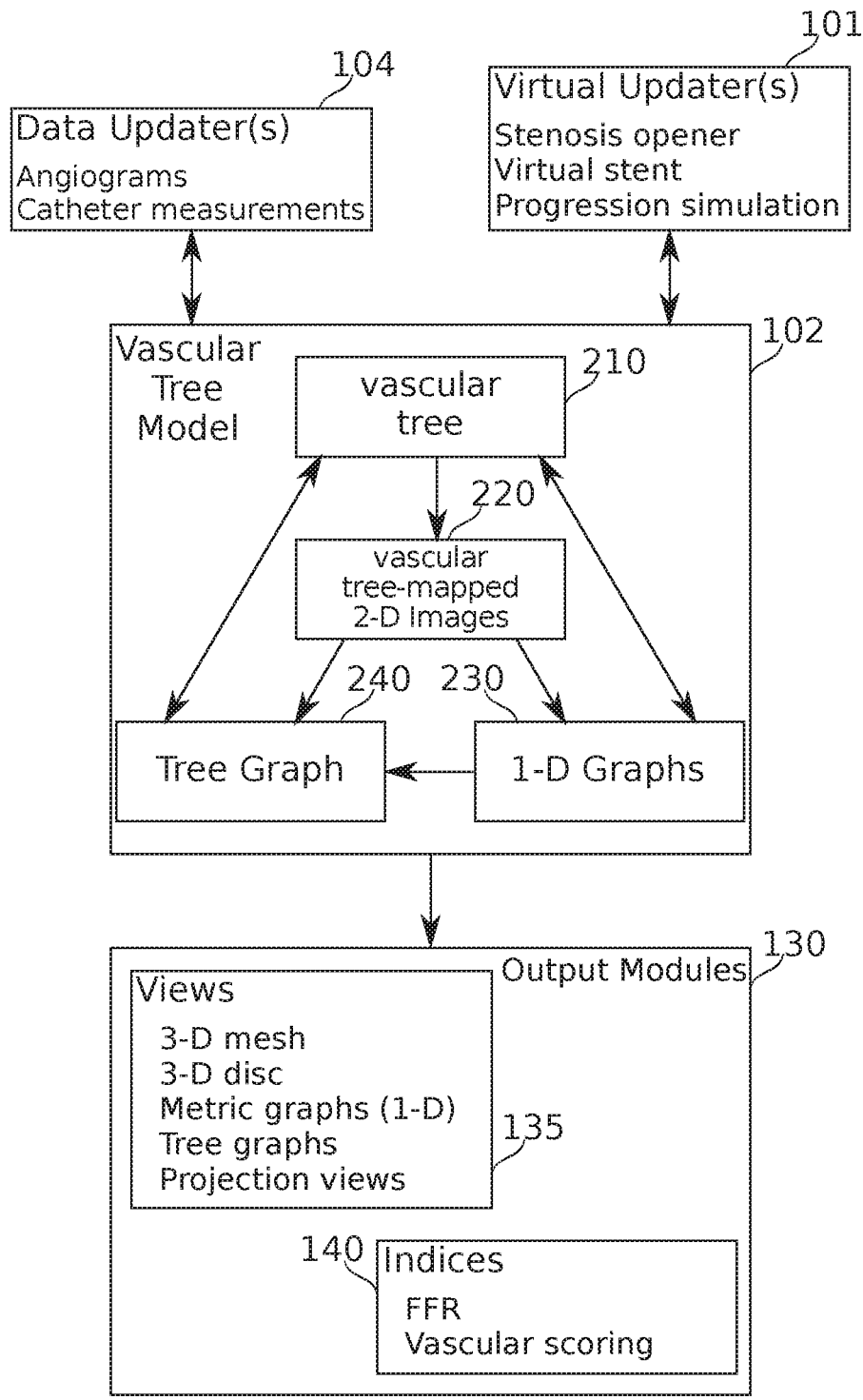
FIG. 2B is a block diagram including particular examples by which some of the blocks of FIG. 2A are realized, according to some exemplary embodiments of the present disclosure.

Reference is now made to FIG. 2A, which is a block diagram of a system 100 for production and use of a dynamically updatable vascular tree model, according to some exemplary embodiments of the present disclosure. Reference is also made to FIG. 2B, which is a block diagram including particular examples by which some of the blocks of FIG. 2A are realized, according to some exemplary embodiments of the present disclosure.

An overview of an embodiment providing an example of a system user interface 150 for use with system 100 is described, for example, in relation to the elements of FIG. 1C. Before introducing additional examples of user interface elements, and in particular overlay and composite displays (for example, in relation to FIGS. 3A-3J), a schematic overview of system 100 and its components is now provided. Such systems and models have been previously described by the inventors in, for example, International Patent Application No. IL2014/050923 filed Oct. 23, 2014 by the Applicant, the contents of which are included herein by reference in their entirety.

In some embodiments, initial image or other data 103 is provided to a vascular tree reconstructor 110, after acquisition by one or more imagers or data acquisition (DAQ) systems 120. In some embodiments, the image data is obtained, for example, by X-ray angiography, and/or from angiographic computed tomography (CT), magnetic resonance imaging (MRI), positron emission tomography (PET), optical coherence tomography (OCT), and/or intravascular ultrasound (IVUS). Optionally, the data provided comprises non-image data related to one or more locations of the vasculature; for example, data acquired from a catheter-mounted sensor and/or radiation source.

In some embodiments, the vascular tree reconstructor 110 reconstructs provided data 103 into a vascular tree model 102 of the vasculature. Herein, the system is described in relation to imaging of vasculature of a mammalian heart—or more specifically a human heart—including, for example, major arteries of the heart. It is to be understood that the system, changed as necessary, is applicable to the modeling of any other vasculature based on the source of the initial data 103.

In some embodiments, the model 102 comprises a plurality of partial and/or complementary representations of the spatial and/or topological (e.g., vascular tree-branch ordered) relationships inherent in the initial data 103.

Representational modes comprise the capability to represent, for example:

a skeletonized (thinned) vascular tree 210 (which may be visually represented, for example, by a branched curing segment tree structure such as tree 310) which follows the routes of vasculature centerlines in two or more dimensions.

2-D images of the vasculature 220 (for example, an image such as angiographic image 503) having homologous regions mapped the vascular tree 210—as provided with the initial data 103 and/or as derived by transformation thereof;

a branched tree graph 240 (which may be visually represented, for example, by an abstracted branch graph display 508) comprising a vascular co-ordinate system corresponding, for example, to lengths and/or branch points of a skeletonized vascular tree 210; and/or 1-D graphs 230 of one or more parameters (e.g., vascular width, curvature, digital FFR, blood pressure, or another parameter) varying along the length of segments of the modeled vascular tree 210.

In some embodiments, a role performed by skeletonized vascular tree 210 in providing a homology map is provided more generally by any data structure that enables determination of homologies among data regions, and the vascular tree-mapped 2-D images are optionally described as homology-mapped 2-D images 220. A data structure that enables determination of homologies comprises, for example, a structure in which parts of the vascular tree are represented, and these part representations are in turn linked to other structures/data types that correspond to the represented part. Vascular tree generation is described, for example, in International Patent Application No. IL2014/050044 filed Jan. 15, 2014 by the Applicant, and/or in International Patent Application No. IL2014/050923 filed Oct. 23, 2014 by the Applicant, the contents of which are included herein by reference in their entirety.

Parts are optionally defined at a level appropriate to the detail required by further calculations that are to be performed. Represented parts of the vascular tree can be, for example, points along the vascular segments (as in a skeletonized tree, a 3-D mesh, or a 3-D volumetric representation), a branched tree structure having nodes and distances (optionally without associated spatial location information), nodes and/or segments as such (with or without further detail such as centerline location), and/or another structure used as a basis for anchoring homology determinations.

In some embodiments, homology is represented without specific reference to a vascular tree representation as such, so that it comprises a "representational mode" only indirectly. For example, homologous data regions are, in some embodiments, tagged, listed, and/or otherwise associated together, optionally without the tags/listings/associations being themselves in direct relationships reflecting position and/or order.

The following examples serve as non-limiting indications of the range of such homology representations contemplated. In embodiments where homology is represented at a fine scale (for example, at about the resolution of the data samples themselves), data structure that directly reflects positions of corresponding anatomical features is potentially advantageous as an organizational scheme (for example, by lending itself well to direct lookup). A skeletonized vascular tree 210 exemplifies this case. In embodiments where homology is represented at a coarse, but still anatomically-anchored scale, a nodal homology structure has potential advantages. For example, vascular segment 2-D centerlines (for instance, vascular centerlines between adjacent bifurcations) are optionally associated as a whole to a specific nodal position in a simplified vascular tree characterized by linked nodes. In some embodiments, homology determination is independent of the global structure of a vascular tree. For example, projection mapping into three dimensions allows determinations of which segment centerlines "belong" together (according, for instance, to general features of proximity and/or orientation), optionally without first, and/or without directly determining the vascular tree relationships of the homology groups themselves.

Accordingly, in some embodiments, the problems of determining global structure, and of determining which data reflect which part of the global structure are optionally treated separately, or in concert, as appropriate to the metric or metrics which are to be calculated.

Updates to the Vascular Tree Model

"Virtual" Updates

In some embodiments, one or more virtual updater modules 101 are provided. A virtual updater module 101 is configured to receive information from vascular model 102, and transform it to create one or more new vascular representations in the mode of one or more of the representational modes of vascular model 102. Optionally, the new representation is passed back to the model and integrated therein—to replace and/or supplement the existing model representation. Optionally or alternatively, a new model is created, and/or the transformed vascular model information is passed directly to an output module 103.

In some embodiments, vascular model 102 exposes 1-D or 2-D data representations of the vasculature to the virtual updater module 101, additionally or alternatively to exposing 3-D representations of the data.

In some embodiments, a virtual updater module 101 comprises (for example) a module configured to perform one or more of the following tasks:

determine an "unstenosed" state of a blood vessel segment, and in particular, an estimate of the geometry of a blood vessel as if a region of stenosis were opened therein;

model an effect on a blood vessel segment due to an insertion of a stent therein;

and/or model changes within a blood vessel segment due to a progression of time.

Modeled blood vessel parameters optionally include, for example, vascular lumen diameter, vascular tortuosity, vascular elasticity, vascular auto-regulatory capacity, vascular wall thickness, flow characteristics, and/or another functional and/or anatomical parameter of the vasculature.

Data Updates

In some embodiments, one or more data updater modules 104 are provided. A data updater module 104 is configured to receive image and/or other data 115 from an imaging means or other DAQ source, and to convert it into a form which can be provided to the vascular model 102. Image data is provided, for example, by X-ray angiography, and/or from CT, MRI, PET, OCT, and/or IVUS. In some embodiments, non-image data is provided, for example, by means of a sensor and/or sensed radiation source advanced through the vasculature on a catheter.

In some embodiments, vascular centerlines are determined for blood vessels identifiable within each of the provided images. Homologies among vascular centerlines in different images are determined, for example, by a method of spatial back-projection, by identification of similarities of vascular branch topology (for example, in comparison to images already assimilated to the model), and/or by identification of similarities in 2-D image vascular appearances (for example, in comparison to images already assimilated to the model). Optionally, estimation of vascular parameters is performed for the new images, for example, by estimation of vascular lumen diameter, tortuosity, or another parameter.

In some embodiments, non-image data is imported to the vascular tree model. For example, in some embodiments, position of a catheter along a vascular segment is known in relation to data acquired by a sensor positioned on the catheter, or by another sensor which detects radiation emitted from a position on the catheter. In such embodiments, data is optionally mapped into the model, for example, directly as a 1-D graph.

Output Modules

In some embodiments, output modules 130 are provided. Optionally, the output modules 130 are divided, for purposes of description, into views 135 and indices 140. Some embodiments of output modules 130 combine functions of each output module type.

In some embodiments, a vascular tree model is viewable as a 3-D model. The 3-D model is, for example, a 3-D disc model, a 3-D mesh model, and/or any other 3-D representation of the data. A 3-D view can be constructed, for example, by combination of a 3-D skeleton with corresponding 1-D graphs of vascular width.

In some embodiments, 1-D metric graphs for display are generated from the 1-D graphs 230 of the vascular tree model. A schematic view of a tree graph 240 can be generated for display, similar, for example, to the abstracted graph display 508. The original images including, for example, angiographic image 503, may be displayed in some embodiments.

In some embodiments, the various views of the representational modes of the vascular tree model are linked together in the viewing interface, which may include a computer screen or projection device. For example, a displayed 3-D model can serve as an anchoring metaphor for navigating the vasculature. Selection of a segment, for example, causes a display of associated 1-D graph information, causes display of highlights for a corresponding segment in a displayed tree graph and/or 2-D image, and/or enables selection for display of one or more 2-D images that comprise representations of the cross-section of the selected vessel.

In some embodiments, an output module 130 comprises a calculation of one or more additional metrics from a vascular tree model, and/or a provision of one or more indexes based on vascular tree model metrics. For example, a fractional flow reserve (FFR) is calculated, in some embodiments, by comparison of a representation of an imaged vasculature that is virtually-updated to an astenotic (open) state with a vasculature as originally imaged. FFR index calculation is described, for example, in International Patent Application No. IL2014/050043, filed Jan. 15, 2014, by the Applicant, the contents of which are included herein by reference in their entirety. Additionally or alternatively, a vascular scoring algorithm is applied to the model to assess clinical situation and provide assistance in selecting a treatment option. Automated vascular scoring is described, for example, in International Patent Application No. IL2013/050889, filed Oct. 24, 2013, by the Applicant, the contents of which are included herein by reference in their entirety. In either case, the contents of the model are optionally updated according to the parameters calculated as part of index determination.

Here and throughout the descriptions, it is to be understood that the described divisions between modules, while convenient for purposes of exposition, do not necessarily correspond to—and do not limit embodiments of the example systems, methods, and/or computer program products to—separation of function in implementation. Functions, methods, and structural details described are optionally comprised within any organizational structure of a system which embodies the disclosure. This includes aspects such as the sources of inputs, the destinations of outputs, and program design patterns. As illustrative examples, the distinction between output modules 130 and virtual updaters 101 is altered in some embodiments to allow: complete combination of the roles of each in a single module, transfer of functions described in connection with one module to the other module, and/or diversion or sharing of output described as provided from a virtual updater module 101 to the model to an output module 130.

Examples of Vascular Overlays and Vascular Composite Images

In some embodiments, one or more types of vascular overlay and/or vascular composite image are provided. FIGS. 3A-3J provide non-limiting examples of information that can be presented in a combined display, based, for example, on the models and/or model transiting methods described in FIGS. 1A-2B.

Vascular Overlays

Figure 3A:
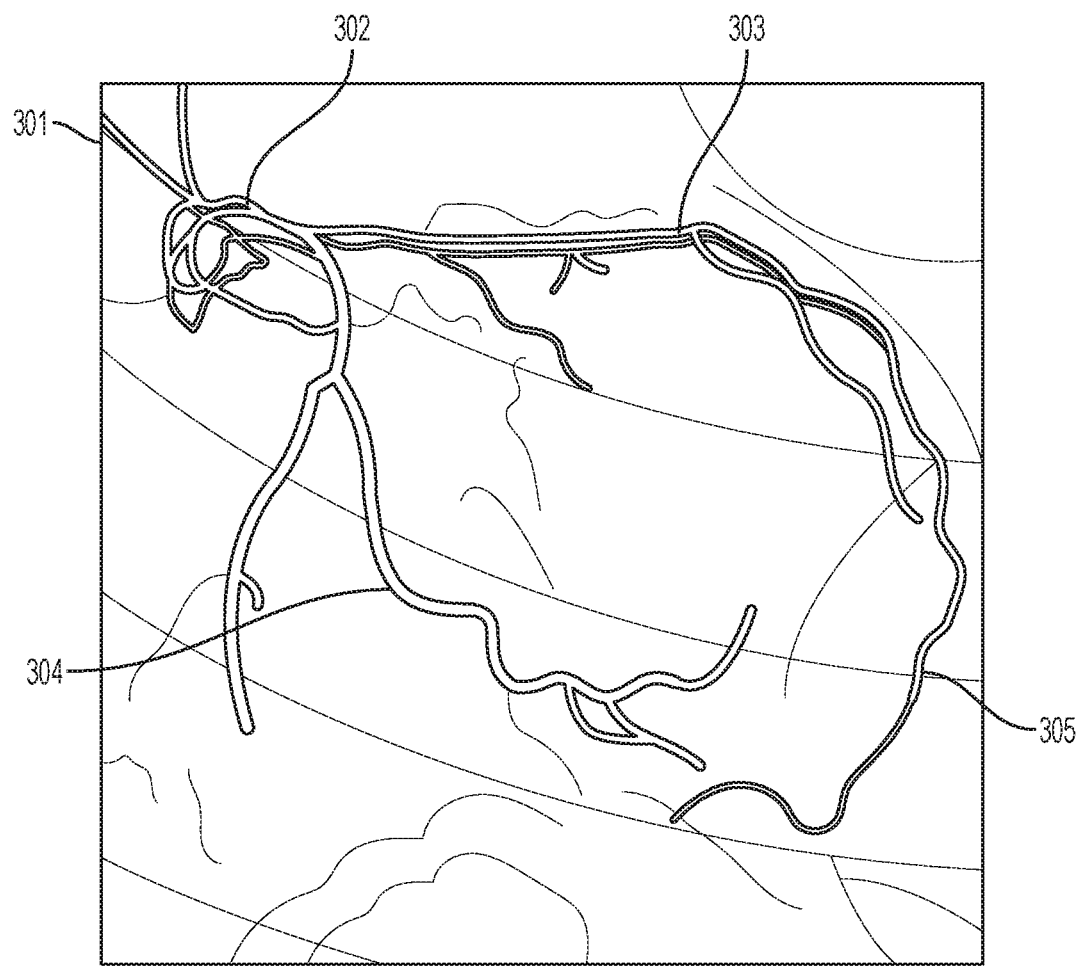
FIG. 3A illustrates an angiogram usable as a base image for data presentation, according to some embodiments of the present disclosure.

Reference is now made to FIG. 3A, which illustrates an angiogram 301 usable as a base image for data presentation, according to some embodiments of the present disclosure. Vascular features of the image 301 of particular note include a coronary artery tree 302 including a number of arterial branches 305 (one particular labeled branch 305 is singled out for purposes of description), and two stenotic or potentially stenotic regions 303, 304.

Figure 3B:
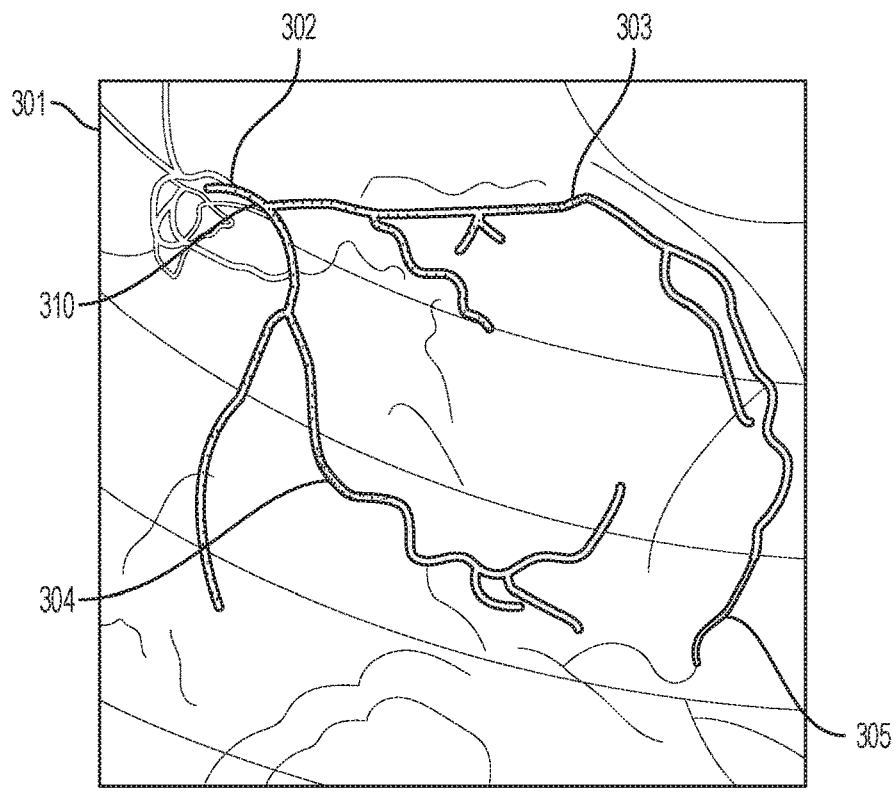
FIGS. 3B, 3C and 3D illustrate angiogram vascular overlays for presentation of auxiliary information along extent of vasculature, according to some embodiments of the present disclosure.
Figure 3C:
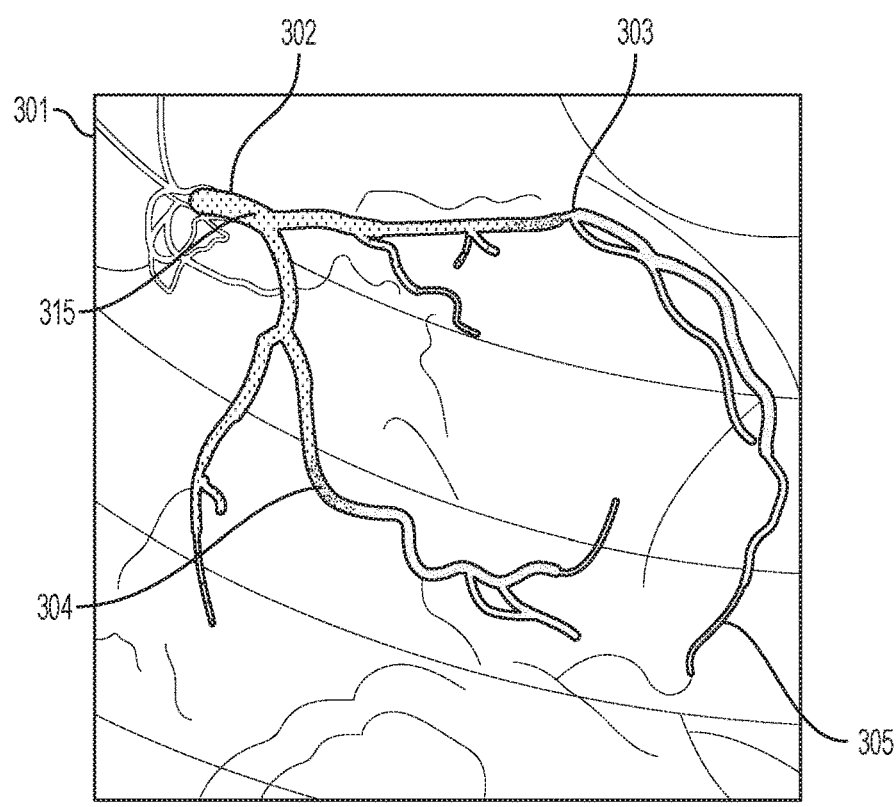
Figure 3D:
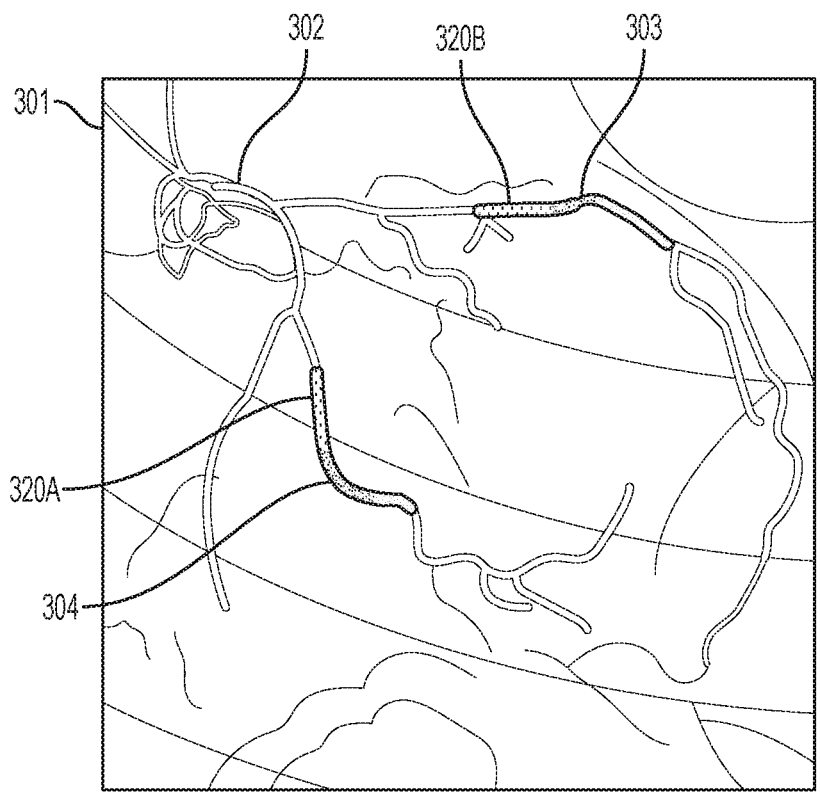

Reference is now made to FIGS. 3B-3D, which illustrate angiogram vascular overlays for presentation of auxiliary information along portions of vasculature, according to some embodiments of the present disclosure.

In FIGS. 3B-3D, a shading-encoded (color-encoded) vascular tree 310 is shown. Color coding is according to a cumulative vascular resistance along each vascular branch. In some embodiments, this is encoded to correspond to display of digital FFR (that is, FFR calculated based on features of the image data). For example, lighter shading and/or yellow indicates FFR values close to 1.00, darker shading and/or red indicate lower FFR values, and regions of shading and/or color transition indicate positions along the arteries where stenosis introduces a reduction in digitally calculated FFR. Vascular width is not encoded in FIG. 3B, but it is encoded in FIGS. 3C-3D (for example, in shading-encoded vascular tree 315 of FIG. 3C) by varying the width along the shaded overlay. In FIG. 3D, regions of low FFR transition are suppressed, so that only a partial shaded overlay is shown, appearing at and/or nearby regions where there is a transition in digital FFR.

It should be understood that FFR is discussed as a parameter for purposes of illustration. In some embodiments, another value which varies along the vascular extent is shading-encoded for display, for example, one of the parameters described in relation to block 12 of FIG. 1A.

Figure 3E:
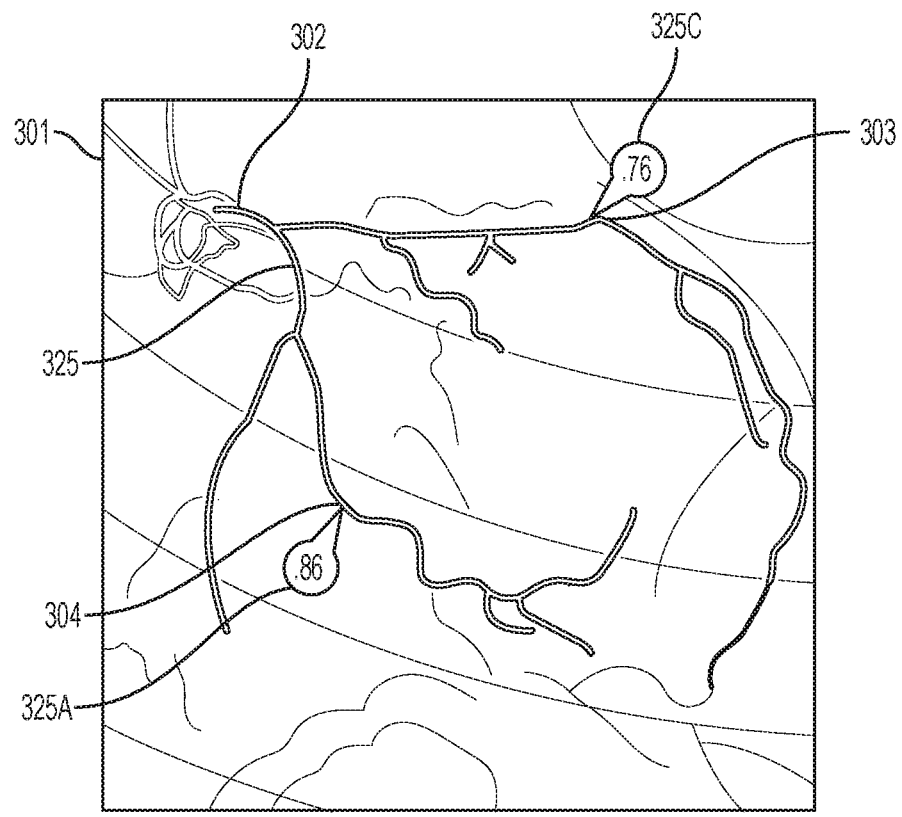
FIG. 3E illustrates angiogram vascular overlays for presentation of auxiliary information as tags, according to some embodiments of the present disclosure.

Reference is now made to FIG. 3E, which illustrate angiogram vascular overlays for presentation of auxiliary information as tags 325A, 325C, according to some embodiments of the present disclosure. In FIG. 3E, the vascular tree 325 is shown without parameter encoding along its width (although optionally, such encoding may be used in combination with tags 325A, 325C, for example, as show in FIG. 1C). In the example shown, tags 325A, 325C indicate FFR values calculated at specific discrete regions 303, 304. Optionally, the FFR values are determined, for example, using a standard pressure probe methodology; for example, a catheter having a pressure sensor is placed upstream and downstream of a stenosis and the pressure ratio converted to an FFR value. Optionally, any other value is shown. Callout-style display is potentially useful, for example, for the display of values that are known only at discrete regions. Additionally or alternatively, callout-style display is provided as a way of indicating numerical values of a parameter at one or more points of interest along the vascular tree.

Figure 3F:
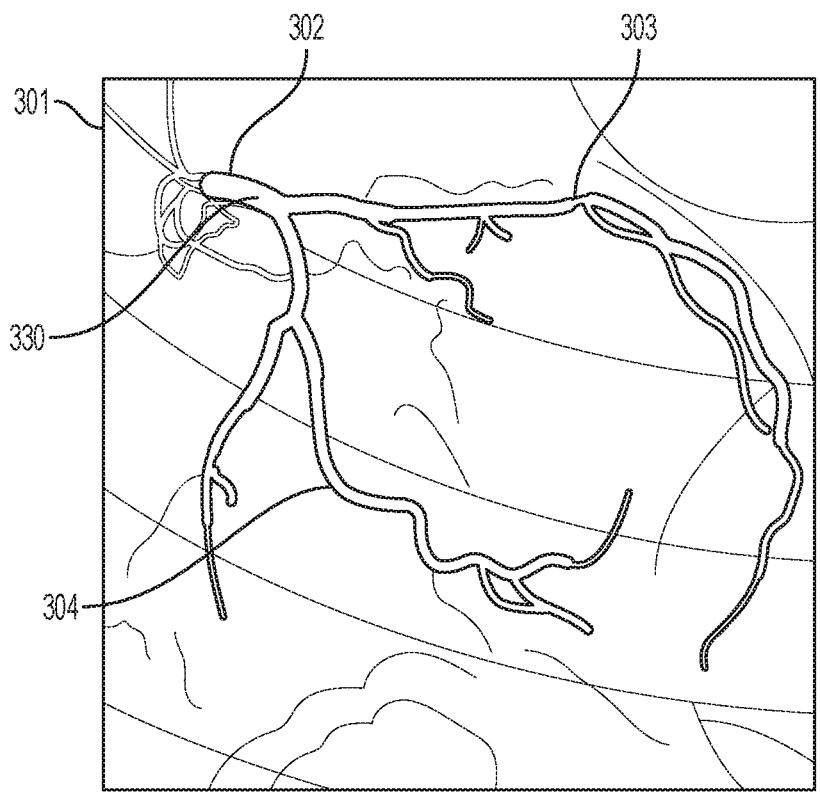
FIGS. 3F and 3G illustrate angiogram vascular overlays for presentation of width information, according to some embodiments of the present disclosure.
Figure 3G:
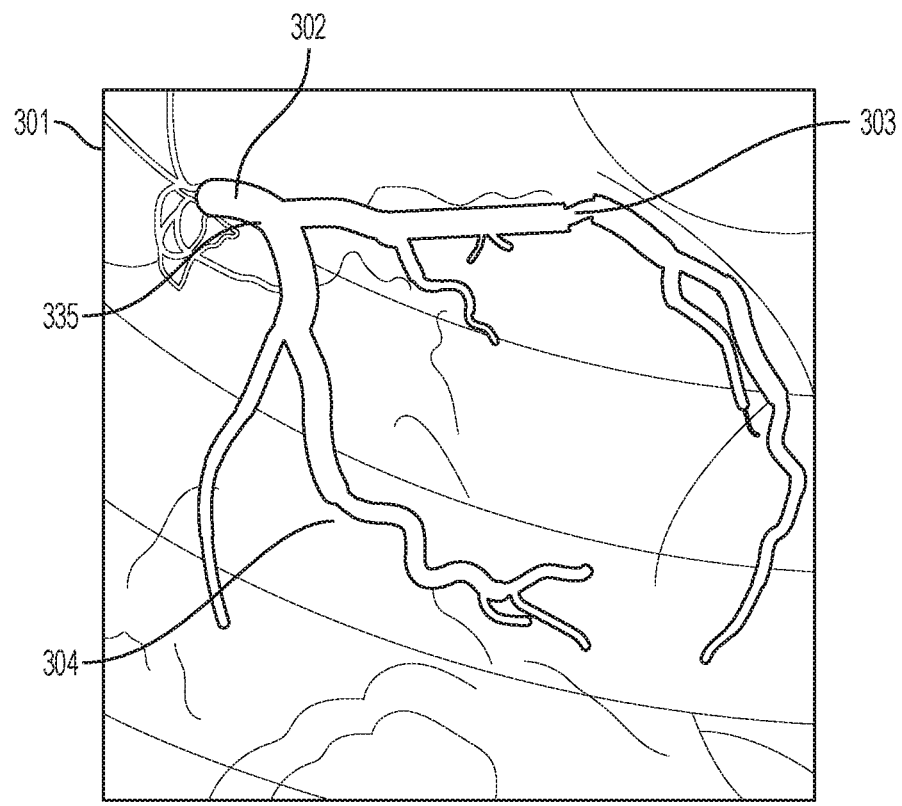

Reference is now made to FIGS. 3F-3G, which illustrate angiogram vascular overlays for presentation of width information, according to some embodiments of the present disclosure. In some embodiments, a vascular overlay 330 is available which visually indicates vascular width corresponding to regions along the vascular image data with which it is displayed. While the image data itself generally also displays vascular width, the overlay provides potential advantages, such as allowing calculated and visual vascular width to be compared, allowing vascular width from one image (for example, from another angle and/or time) to be readily compared to another, and/or to act as a high-contrast display of the original data.

Another optional feature of a width overlay is shown as vascular tree 335 of FIG. 3G. In some embodiments, display vascular width is optionally scaled differently than longitudinal vascular extent. For example, vascular tree 335 shows double-scaled vascular width. A potential advantage of this is to allow easier visual identification of stenotic regions, for example, at regions 303 and/or 304.

Vascular Composite Images

Figure 3H:
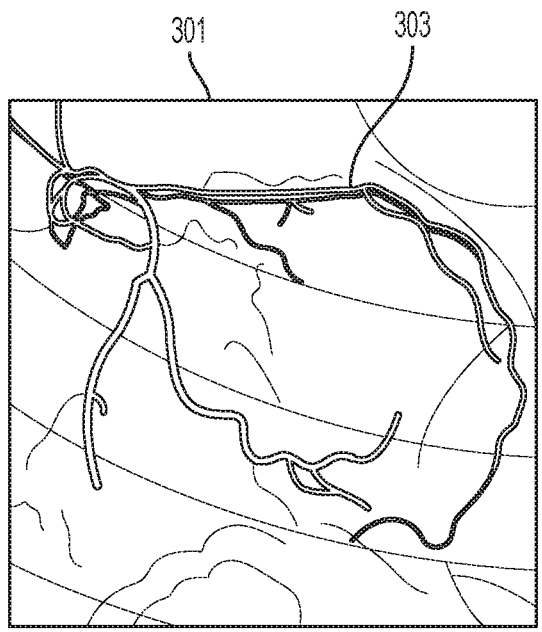
FIGS. 3H and 3I illustrate angiograms comprising first and second states of a cardiac vasculature, according to some embodiments of the present disclosure.
Figure 3I:
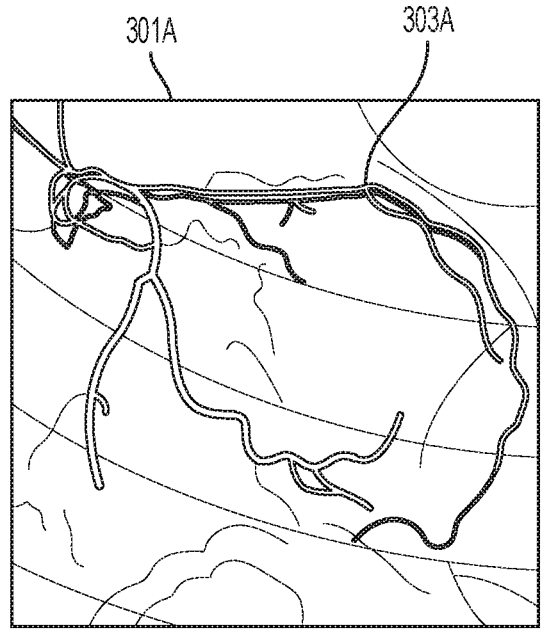
Figure 3J:
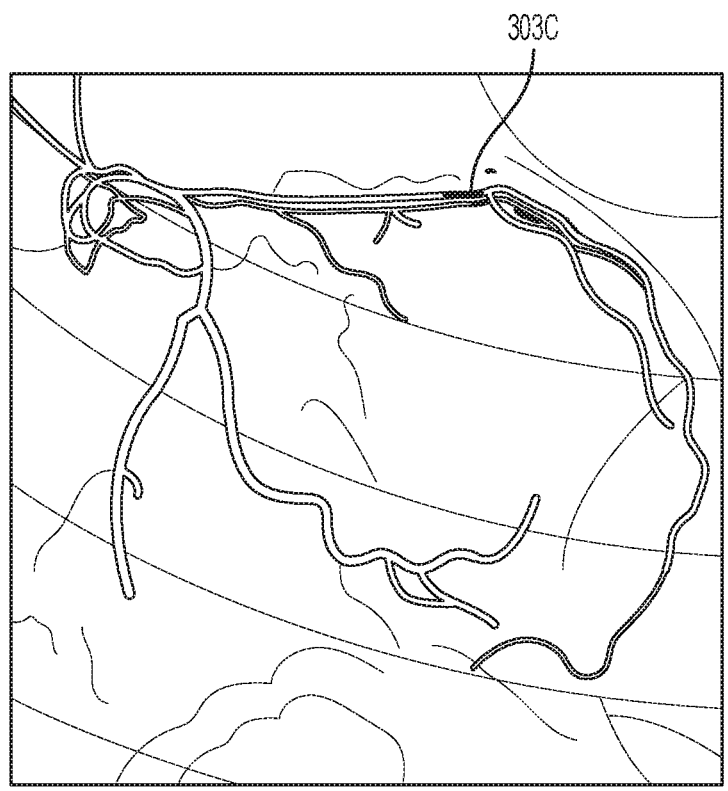
FIG. 3J is a schematic representation of a differential analysis display of the angiograms of FIGS. 3H-3I, according to some embodiments of the present disclosure.

Reference is now made to FIGS. 3H-3I, which illustrate angiograms comprising first and second states of a cardiac vasculature, according to some embodiments of the present disclosure. Reference is also made to FIG. 3J, which is a schematic representation of a differential analysis display of the angiograms of FIGS. 3H-3I, according to some embodiments of the present disclosure.

In some embodiments, a composited display (for example, as shown in FIG. 3J) comprises a combination of two or more vascular images. Optionally, the images are raw images (for example, images taken at different times), which have been registered to one another. In some embodiments, one or more of the images is at least partially synthesized. For example, the image 301A of FIG. 3I optionally represents a synthetically revascularized version of the image 301 of FIG. 3H. An example of a method of synthetic revascularization is described, for example, in relation to FIGS. 4A-4B.

In some embodiments, the two or more images are subjected to one or more compositing operations. Such compositing operations optionally include, for example, addition, subtraction, division, multiplication, transparency overlay, color channel mapping overlay, masking, and/or another image processing technique for combining images. Optionally such operations are applied, for example, in combination with one or more techniques of filtering, normalization, noise reduction, and/or other image processing techniques.

A region of difference between two images is illustrated by region 303 (of FIG. 3H), compared to region 303A (of FIG. 3I). Region 303 is stenotic, while region 303A is not. FIG. 3J has been composited so that differences between the two images are emphasized at region 303C. Such a composite display is potentially useful for isolating changes in a vasculature over time, and/or in two different conditions (for example, with and without the effects of adenosine injection). Relevant changes in vasculature over time optionally include, for example, changes in vascular width and/or changes in vascular position, for example due to changes in curvature, tortuosity and/or development of vascular collaterals.

Potentially, such a composite display is used to indicate modeled effects of disease treatment and/or progression, for example based on the use of one or more synthetic images.

Method of Simulating Modified Vascular Appearance

Figure 4A:
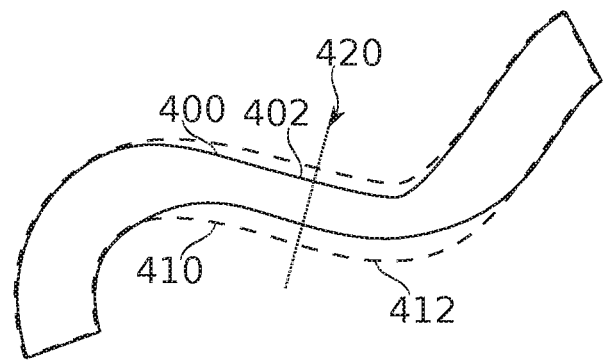
FIGS. 4A and 4B schematically illustrate a method of modifying an angiogram image to adjust an apparent vascular width shown thereon, according to some embodiments of the present disclosure.
Figure 4B:
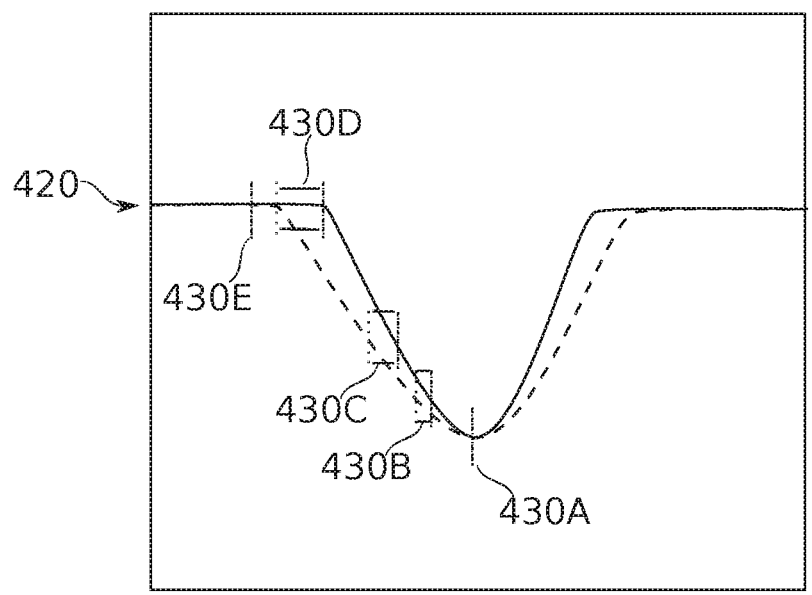

Reference is now made to FIGS. 4A-4B, which schematically illustrate a method of modifying an angiogram image to adjust an apparent vascular width shown thereon, according to some embodiments of the present disclosure.

Shown in FIG. 4A is a schematic representation of an identified vascular profile 410, for example one obtained from an image of a blood vessel coursing through a vascular image (such as vascular image 301). Vascular profile 400, in some embodiments, comprises vascular widths specified along a range of vascular positions 402. In some embodiments, a synthetic profile 410 is generated along a range of vascular positions 412 which are in correspondence with positions 402. As shown, the synthetic profile 410 is wider than the source profile, and optionally represents a revascularization (for example, as obtained after insertion of a stent, or by another treatment). Optionally synthetic profile 410 is narrower, for example to represent effects of a disease progression.

In some embodiments, a copy of the image from which profile 400 was originally obtained is modified to reflect features of synthetic profile 410. Such an instance is shown, for example, in comparing regions 303 and 303A of FIGS. 3H-3I. In some embodiments, the modification is performed by stretching or shrinking pixel value profiles along profiles such as profile 420. In FIG. 4B, an example of profile stretching is shown. Position along the profile is shown on the horizontal axis, and relative pixel value is shown on the vertical axis. At position 430A, there is no difference between the stretched and unstretched profiles. Moving outward to profile positions 430B, 430C, and 430D, pixel values are increasingly displaced (with interpolation between them) to simulate a wider vascular profile. By the point of position 430E, the stretching factor is returned to zero.

In some embodiments, another synthetic vascular width adjustment method is used, for example, based on the assumption of a circular (typically, but not only) profile and the application of densitometry principles to more accurately simulate changes in the radiopacity profile as a result of vascular width changes.

A potential advantage of synthetic vascular angiography images is their optional use as direct inputs to algorithms which are applicable to raw vascular images. Another potential advantage is to allow more direct visual assessment of anticipated changes as a result of disease treatment or progression to actual changes. For example, comparison of a partially synthetic angiographic image of a condition to an image of the actual condition is potentially useful to a clinician used to seeing and evaluating patient status based on original image data.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the example systems, methods, and/or computer program products may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of the example systems, methods, and/or computer program products may be presented with reference to a range format. It should be understood that the description in range format is merely for convenience and brevity and should not be construed as an inflexible limitation on the scope of the systems, methods, and/or computer program products. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the example systems, methods, and/or computer program products have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features of the example systems, methods, and/or computer program products, which are, for clarity, described in the context of separate embodiments, may also be provided in combination in a single embodiment. Conversely, various features of the example systems, methods, and/or computer program products, which are, for brevity, described in the context of a single embodiment, may also be provided separately or in any suitable subcombination or as suitable in any other described embodiment of the example systems, methods, and/or computer program products. Certain features described in the context of various embodiments are not to be considered essential features of those embodiments, unless the embodiment is inoperative without those elements.

The invention is claimed as follows:

1. A method for displaying vascular parameter data, the method comprising:

receiving, in a processor, a first 2-D angiographic image recorded at a first angle with respect to a patient containing a first image representation of the patient's coronary arteries and a second 2-D angiographic image recorded at a second angle with respect to the patient containing a second image representation of the patient's coronary arteries, the second angle being at least 30° different from the first angle;

creating, via the processor, a first data structure including first coordinates that are indicative of vascular locations of the patient's coronary arteries in the first 2-D angiographic image and a second data structure including second coordinates that are indicative of the vascular locations of the patient's coronary arteries in the second 2-D angiographic image;

creating, via the processor, a third data structure including identifiers that are each representative of the vascular locations along the patient's coronary arteries, each identifier being linked to a coordinate of the first coordinates and a corresponding coordinate of the second coordinates that correspond to a same vascular location of the patient's coronary arteries;

creating, via the processor, a fourth data structure including vascular parameter data that is linked to corresponding identifiers of the third data structure based on locations of the identifiers corresponding to the vascular locations of the patient's coronary arteries;

determining, via the processor, the vascular locations where at least some of the vascular parameter data is to be displayed in relation to the first 2-D angiographic image using the identifiers in the third data structure that link the vascular parameter data to the first coordinates; and displaying via the processor, the first 2-D angiographic image and the at least some of the vascular parameter data such that the at least some of the vascular parameter data is displayed in proximity to a corresponding vascular location of the patient's coronary arteries shown in the first 2-D angiographic image.

2. The method of claim 1, further comprising receiving, in the processor, a selection of the first angiographic image before determining the vascular locations where at least some of the vascular parameter data is to be displayed in relation to the first 2-D angiographic image.

3. The method of claim 1, wherein linking the identifiers within at least one of the third data structure or the fourth data structure includes storing information indicative of the vascular locations in association with respective identifying tags.

4. The method of claim 1, wherein linking the identifiers within at least one of the third data structure or the fourth data structure includes storing information indicative of the vascular locations in association within a list.

5. The method of claim 4, wherein the list is an ordered list.

6. The method of claim 5, wherein linking the identifiers includes using a position that is specified relative to other vascular locations or elements of the ordered list.

7. The method of claim 1, wherein the display of the at least some of the vascular parameter data at the vascular locations includes rendering a path between some of the vascular locations, the path being rendered with widths based on values determined by processing vascular widths for the vascular locations of at least one of the first 2-D angiographic image or the second 2-D angiographic image.

8. The method of claim 7, wherein the widths are rendered by at least 1.5 times greater scale than the scale of a vascular diameter in a frame of reference of the first 2-D angiographic image.

9. The method of claim 1, wherein the display of the at least some of the vascular parameter data at the vascular locations includes rendering a path between the vascular locations, the path having a color assigned based on values of the at least some of the vascular parameter data.

10. The method of claim 1, wherein the display of the at least some of the vascular parameter data at the vascular locations includes rendering a path between the vascular locations, the path having at least one of a transparency or a gap assigned based on values of the at least some of the vascular parameter data.

11. The method of claim 1, wherein the display of the at least some of the vascular parameter data at each of the vascular locations is based on a plurality of accessed parameter data elements.

12. The method of claim 11, wherein at least one of the third data structure or the fourth data structure additionally links at least a third 2-D angiographic image not registrable to consistently align with the first and second 2-D angiographic images by an invertible 2-D geometrical transform, and at least some values of the accessed parameter data elements are derived from processing of the vascular locations of the third 2-D angiographic image.

13. The method of claim 11, wherein the display of the at least some of the vascular parameter data at the vascular locations includes rendering using any combination of displayed path width, display color, display transparency, or display color channel assignment.

14. The method of claim 11, wherein the plurality of accessed parameter data elements represent a same vascular parameter for a plurality of parameter values.

15. The method of claim 14, wherein the plurality of parameter values includes values representing a vasculature in different states.

16. The method of claim 11, wherein the display of the at least some of the vascular parameter data at each of the vascular locations alternates between being based on different element accessed vascular parameter data.

17. The method of claim 1, wherein image contents of at least one of the first and the second 2-D angiographic images include views of a vasculature recorded at different view angles.

18. The method of claim 1, wherein image contents of at least one of the first and the second 2-D angiographic images include views of a vasculature in at least two respective different anatomical states.

19. An apparatus for display of vascular parameters for vascular assessment, the apparatus comprising:
  a memory device storing:
    a first angiographic image recorded at a first angle with respect to a patient containing a first image representation of the patient's coronary arteries,
    a second angiographic image recorded at a second angle with respect to the patient containing a second image representation of the patient's coronary arteries, the second angle being at least 30° different from the first angle,
    a first data structure including first coordinates that are indicative of vascular locations of the patient's coronary arteries in the first angiographic image,
    a second data structure including second coordinates that are indicative of the vascular locations of the patient's coronary arteries in the second angiographic image,
    a third data structure including identifiers that are each representative of the vascular locations along the patient's coronary arteries, each identifier being linked to a coordinate of the first coordinates and a corresponding coordinate of the second coordinates that correspond to a same vascular location of the patient's coronary arteries, and
    a fourth data structure including vascular parameter data that is linked to corresponding identifiers of the third data structure based on locations of the identifiers-along corresponding to the vascular locations of the patient's coronary arteries; and a processor communicatively coupled to a memory device, the processor configured to:
  determine vascular locations where at least some of the vascular parameter data is to be displayed in relation to the first angiographic image using the identifiers in the third data structure that link the vascular parameter data to the first coordinates, and
  cause the first angiographic image and the at least some of the vascular parameter data to be displayed such that the at least some of the vascular parameter data is displayed in proximity to a corresponding vascular location of the patient's coronary arteries shown in the first angiographic image.

20. The apparatus of claim 19, wherein the processor is configured to receive a selection of the first angiographic image before determining the vascular locations where at least some of the vascular parameter data is to be displayed in relation to the first 2-D angiographic image.

21. The apparatus of claim 19, wherein the processor is configured to:
  receive a selection of the second angiographic image;
  determine the vascular locations where at least some of the vascular parameter data is to be displayed in relation to the second angiographic image using the identifiers in the third data structure that link the vascular parameter data to the second coordinates; and
  cause the second angiographic image and the at least some of the vascular parameter data to be displayed such that the at least some of the vascular parameter data is displayed in proximity to a corresponding vascular location of the patient's coronary arteries shown in the second angiographic image.

22. The apparatus of claim 21, wherein the processor is configured to cause the first angiographic image and the at least some of the vascular parameter data to be removed from display.

23. The apparatus of claim 21, wherein the processor is configured to:
  cause the at least some of the vascular parameter data to be displayed in a first frame of reference corresponding to the first angiographic image; and
  cause the at least some of the vascular parameter data to be displayed in a second frame of reference corresponding to the second angiographic image.

24. The apparatus of claim 19, wherein the processor is configured to:
  create a graphical representation of the patient's coronary arteries using the first coordinates; and
  display the graphical representation instead of the first angiographic image.

25. The apparatus of claim 19, wherein the second angiographic image is adjusted to have at least one of a same scale or orientation as the first angiographic image such that the first coordinates have a same scale or orientation as the second coordinates.

26. The apparatus of claim 19, wherein the vascular locations along the patient's coronary arteries include at least one of continuous points or sparse points along the patient's coronary arteries.

27. The apparatus of claim 19, wherein the vascular parameter data includes at least one of blood pressure values, blood flow resistance values, plaque burden values, fractional flow reserve ("FFR") values, flow velocity values, perfusion information, tissue territory information, vascular deformation information, or SYNTAX score values.

* * * * *